(12) United States Patent
Wiebe et al.

(10) Patent No.: US 10,785,980 B2
(45) Date of Patent: Sep. 29, 2020

(54) SUBSTITUTED OXADIAZOLES FOR COMBATING PHYTOPATHOGENIC FUNGI

(71) Applicant: BASF SE, Ludwigshafen am Rhein (DE)

(72) Inventors: Christine Wiebe, Ludwigshafen (DE); Violeta Terteryan-Seiser, Ludwigshafen (DE); Wassilios Grammenos, Ludwigshafen (DE); Ian Robert Craig, Ludwigshafen (DE); Maria Angelica Quintero Palomar, Limburgerhof (DE); Tobias Mentzel, Limburgerhof (DE); Marcus Fehr, Limburgerhof (DE); Christian Harald Winter, Ludwigshafen (DE); Erica Cambeis, Sale (GB); Jan Klaas Lohmann, Ludwigshafen (DE); Ana Escribano Cuesta, Ludwigshafen (DE); Manuel Kretschmer, Washington, DC (US); Thomas Grote, Ludwigshafen (DE); Bernd Mueller, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/306,294

(22) PCT Filed: May 31, 2017

(86) PCT No.: PCT/EP2017/063207
§ 371 (c)(1),
(2) Date: Nov. 30, 2018

(87) PCT Pub. No.: WO2017/211649
PCT Pub. Date: Dec. 14, 2017

(65) Prior Publication Data
US 2019/0216088 A1   Jul. 18, 2019

(30) Foreign Application Priority Data
Jun. 9, 2016   (EP) .................................... 16173718

(51) Int. Cl.
| | | |
|---|---|---|
| *A01N 43/88* | (2006.01) | |
| *C07D 413/04* | (2006.01) | |
| *C07D 271/107* | (2006.01) | |
| *A61P 31/10* | (2006.01) | |
| *A01N 43/10* | (2006.01) | |
| *C07D 271/06* | (2006.01) | |
| *A01N 43/82* | (2006.01) | |
| *A01N 53/00* | (2006.01) | |

(52) U.S. Cl.
CPC .......... *A01N 43/88* (2013.01); *A01N 43/10* (2013.01); *A01N 43/82* (2013.01); *A01N 53/00* (2013.01); *A61P 31/10* (2018.01); *C07D 271/06* (2013.01); *C07D 271/107* (2013.01); *C07D 413/04* (2013.01)

(58) Field of Classification Search
None
See application file for complete search history.

(56) References Cited

U.S. PATENT DOCUMENTS

| 4,871,753 A | 10/1989 | Rohr |
| 2003/0224936 A1 | 12/2003 | Kretzschmar |

FOREIGN PATENT DOCUMENTS

| CL | 2018000832 A1 | 7/2018 |
| CL | 2018000834 A1 | 7/2018 |
| CN | 1927860 A | 3/2007 |
| EP | 0276432 A2 | 8/1988 |
| EP | 1329160 A2 | 7/2003 |
| EP | 3165093 A1 | 5/2017 |
| EP | 3165094 A1 | 5/2017 |
| EP | 3167716 A1 | 5/2017 |
| WO | 9405153 A1 | 3/1994 |
| WO | 9715576 A1 | 5/1997 |
| WO | 9730047 A1 | 8/1997 |
| WO | 03059903 A2 | 7/2003 |

(Continued)

OTHER PUBLICATIONS

Office action, issued in co-pending U.S. Appl. No. 15/773,293, dated Apr. 2, 2019.

(Continued)

*Primary Examiner* — Kamal A Saeed
(74) *Attorney, Agent, or Firm* — Marshall, Gerstein & Borun LLP

(57) ABSTRACT

The present invention relates to novel trifluoromethyl oxadiazoles of the formula I, or an N-oxide, and/or their agriculturally useful salts; to their use for controlling phytopathogenic fungi; to a method for combating phytopathogenic harmful fungi, which process comprises treating the fungi or the plants, the soil or seeds to be protected against fungal attack, with an effective amount of at least one compound of the formula I, or an N-oxide, or an agriculturally acceptable salt thereof; to agrochemical compositions comprising at least one such compound; and to agrochemical compositions further comprising seeds.

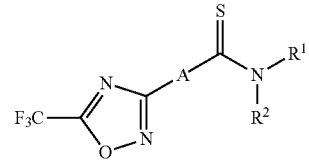

20 Claims, No Drawings

(56) References Cited

FOREIGN PATENT DOCUMENTS

| | | |
|---|---|---|
| WO | 04020445 A2 | 3/2004 |
| WO | 05040152 A1 | 5/2005 |
| WO | 06102645 A1 | 9/2006 |
| WO | 13006408 A1 | 1/2013 |
| WO | 13008162 A1 | 1/2013 |
| WO | 13064079 A1 | 5/2013 |
| WO | 13066835 A2 | 5/2013 |
| WO | 13066839 A2 | 5/2013 |
| WO | 15086462 A1 | 6/2015 |
| WO | 15173050 A1 | 11/2015 |
| WO | 15181035 A1 | 12/2015 |
| WO | 15185485 A1 | 12/2015 |
| WO | 15185708 A1 | 12/2015 |
| WO | 15189035 A1 | 12/2015 |
| WO | 15197458 A1 | 12/2015 |
| WO | 16055404 A1 | 4/2016 |
| WO | 16142224 A1 | 9/2016 |
| WO | 16156129 A1 | 10/2016 |
| WO | 16166020 A1 | 10/2016 |
| WO | 17016915 A1 | 2/2017 |
| WO | 17055469 A1 | 4/2017 |
| WO | 17055473 A1 | 4/2017 |
| WO | 17055587 A1 | 4/2017 |
| WO | 17060148 A1 | 4/2017 |
| WO | 17067784 A1 | 4/2017 |
| WO | 17076739 A1 | 5/2017 |
| WO | 17076740 A1 | 5/2017 |
| WO | 17076742 A1 | 5/2017 |
| WO | 17076757 A1 | 5/2017 |
| WO | 17076935 A1 | 5/2017 |
| WO | 17081309 A1 | 5/2017 |
| WO | 17081310 A1 | 5/2017 |
| WO | 17081311 A1 | 5/2017 |
| WO | 17081312 A1 | 5/2017 |
| WO | 17085098 A1 | 5/2017 |
| WO | 17085100 A1 | 5/2017 |
| WO | 17093019 A1 | 6/2017 |
| WO | 17093120 A1 | 6/2017 |
| WO | 17093167 A1 | 6/2017 |
| WO | 17148797 A1 | 9/2017 |
| WO | WO-2017162868 | 9/2017 |
| WO | 17178245 A1 | 10/2017 |
| WO | 17211650 A1 | 12/2017 |
| WO | 17211652 A1 | 12/2017 |

OTHER PUBLICATIONS

Office Action, issued in co-pending U.S. Appl. No 15/777,281, dated Jan. 8, 2019.
International Search Report, dated PCT/EP2017/063207, dated Jul. 11, 2017.
International Preliminary Report on Patentability, issued in PCT/EP2017/063207, dated Dec. 11, 2018.

SUBSTITUTED OXADIAZOLES FOR COMBATING PHYTOPATHOGENIC FUNGI

This application is a National Stage application of International Application No. PCT/EP2017/063207, filed May 31, 2017. This application also claims priority under 35 U.S.C. § 119 to European Patent Application No. 16173718.4, filed Jun. 9, 2016.

The present invention relates to novel trifluoromethyl oxadiazoles of the formula I, or an N-oxide, and/or their agriculturally useful salts; to their use for controlling phytopathogenic fungi; to a method for combating phytopathogenic harmful fungi, which process comprises treating the fungi or the plants, the soil or seeds to be protected against fungal attack, with an effective amount of at least one compound of the formula I, or an N-oxide, or an agriculturally acceptable salt thereof; to agrochemical compositions comprising at least one such compound; and to agrochemical compositions further comprising seeds.

WO 2017/055469 A1 and WO 2017/055473 A1 describe derivatives of trifluoromethyl-oxadiazoles and their use to combat phytopathogenic microorganisms. WO 2015/185485 A1 describes similar derivatives of trifluoromethyl-oxadiazoles and relates to their use for combating phytopathogenic microorganisms. EP 276432 A2 relates to 3-phenyl-5-trifluoromethyloxadiazole derivatives and to their use for combating phytopathogenic microorganisms. WO 97/30047 A1 describes certain trifluoromethyloxadiazole analogues with fungicidal activity, wherein the trifluoromethyloxadiazole group and an amide functional group are attached to a phenyl ring in an ortho-relationship.

In many cases, in particular at low application rates, the fungicidal activity of known fungicidal compounds is unsatisfactory. Based on this, it was an object of the present invention to provide compounds having improved activity and/or a broader activity spectrum against phytopathogenic fungi. This objective is achieved by the use of oxadiazoles of the formula I and/or their agriculturally useful salts for controlling phytopathogenic fungi.

Accordingly, the present invention relates to compounds of the formula I, or the N-oxides, or the agriculturally acceptable salts thereof,

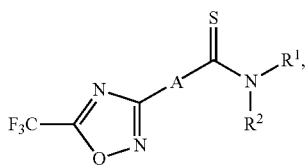

I wherein:
A is phenyl or thiophenyl; and wherein the cyclic groups A are unsubstituted or substituted with 1, 2, 3 or 4 identical or different groups $R^A$; wherein
 $R^A$ is OH, cyclopropyl, halogen, cyano, di$C_1$-$C_6$-alkylamino, $C_1$-$C_6$-alkyl, $C_1$-$C_6$-alkoxy, $C_1$-$C_6$-alkylthio, $C_2$-$C_6$-alkenyl, $C_2$-$C_6$-alkynyl, $C_3$-$C_8$-cycloalkyl or $C_3$-$C_8$-cycloalkoxy; and wherein any of the aliphatic or cyclic moieties are unsubstituted or substituted with 1, 2, 3 or 4 identical or different groups $R^a$; wherein
  $R^a$ is halogen, cyano, $C_1$-$C_6$-alkyl, $C_1$-$C_6$-haloalkyl, $C_1$-$C_6$-alkoxy or $C_1$-$C_6$-haloalkoxy;
$R^1$, $R^2$ independently of each other are hydrogen, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, $C_1$-$C_4$-alkoxy, —C(=O)—($C_1$-$C_6$-alkyl), —C(=O)—($C_1$-$C_6$-alkoxy), phenyl-$C_1$-$C_4$-alkyl, heteroaryl-$C_1$-$C_4$-alkyl, $C_3$-$C_6$-cycloalkyl-$C_1$-$C_4$-alkyl, phenyl, naphthyl or a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms and wherein 1 or 2 carbon ring member atoms of the heterocycle may be replaced by 1 or 2 groups independently selected from —C(=O)— and —C(=S)—; and wherein the heteroaryl group in heteroaryl-$C_1$-$C_4$-alkyl is a 5- or 6-membered aromatic heterocycle, wherein the ring member atoms of the heterocyclic ring include besides carbon atoms 1, 2, 3 or 4 heteroatoms selected from N, O and S as ring member atoms; and wherein any of the above-mentioned aliphatic or cyclic groups are unsubstituted or substituted with 1, 2, 3 or up to the maximum possible number of identical or different groups $R^{1a}$;
or $R^1$ and $R^2$ together with the nitrogen atom to which they are bound form a saturated or partially unsaturated mono- or bicyclic 3- to 10-membered heterocycle, wherein the heterocycle includes beside one nitrogen atom and one or more carbon atoms 1, 2 or 3 heteroatoms independently selected from N, O and S as ring member atoms; and wherein one or two $CH_2$ groups of the heterocycle may be replaced by one or two groups independently selected from the group of —C(=O)— and —C(=S)—; and wherein the heterocycle is unsubstituted or substituted with 1, 2, 3, 4 or up to the maximum possible number of identical or different groups $R^{1a}$; wherein
 $R^{1a}$ is halogen, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, —$NHSO_2$—$C_1$-$C_4$-alkyl, —(C=O)$C_1$-$C_4$-alkyl, —C(=O)—$C_1$-$C_4$-alkoxy or $C_1$-$C_6$-alkylsulfonyl, hydroxy$C_1$-$C_4$-alkyl, —C(=O)—$NH_2$, —C(=O)—NH($C_1$-$C_4$-alkyl), $C_1$-$C_4$-alkylthio-$C_1$-$C_4$-alkyl, amino$C_1$-$C_4$-alkyl, $C_1$-$C_4$-alkylamino-$C_1$-$C_4$-alkyl, di$C_1$-$C_4$-alkylamino-$C_1$-$C_4$-alkyl, aminocarbonyl-$C_1$-$C_4$-alkyl or $C_1$-$C_4$-alkoxy-$C_1$-$C_4$-alkyl.

Agriculturally useful salts of the compounds I encompass especially the salts of those cations or the acid addition salts of those acids whose cations and anions, respectively, have no adverse effect on the fungicidal action of the compounds I. Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may be substituted with one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound I with an acid of the corresponding anion, preferably of hydrochloric acid, hydrobromic acid, sulfuric acid, phosphoric acid or nitric acid.

Compounds I can exist as one or more stereoisomers. The various stereoisomers include enantiomers, diastereomers, atropisomers arising from restricted rotation about a single bond of asymmetric groups and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers.

The compounds of the invention may be present as a mixture of stereoisomers, e.g. a racemate, individual stereoisomers, or as an optically active form.

Compounds of formula I can be present in different crystal modifications whose biological activity may differ. They also form part of the subject matter of the present invention. The compounds of formula I can be present in atropisomers arising from restricted rotation about a single bond of asymmetric groups. They also form part of the subject matter of the present invention.

In respect of the variables, the embodiments of the intermediates obtained during preparation of compounds I correspond to the embodiments of the compounds of formula I. The term "compounds I" refers to compounds of formula I.

In the definitions of the variables given above, collective terms are used which are generally representative for the substituents in question. The term "$C_n$-$C_m$" indicates the number of carbon atoms possible in each case in the substituent or substituent moiety in question.

The moieties having two ore more possibilities to be attached apply following:

The moieties having no brackets in the name are bonded via the last moiety e.g. heteroaryl-$C_1$-$C_4$-alkyl is bonded via $C_1$-$C_4$-alkyl. etc.

The moieties having brackets in the name are bonded via the first moiety e.g. C(=O)—($C_1$-$C_6$-alkyl) is bonded via C=O, etc.

The term "halogen" refers to fluorine, chlorine, bromine and iodine.

The term "$C_1$-$C_6$-alkyl" refers to a straight-chained or branched saturated hydrocarbon group having 1 to 6 carbon atoms, for example methyl, ethyl, propyl, 1-methylethyl, butyl, 1-methylpropyl, 2-methylpropyl, and 1,1-dimethylethyl.

The term "$C_1$-$C_6$-haloalkyl" refers to a straight-chained or branched alkyl group having 1 to 6 carbon atoms (as defined above), wherein some or all of the hydrogen atoms in these groups may be replaced by halogen atoms as mentioned above, for example chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2$—$C_2F_5$, $CF_2$—$C_2F_5$, $CF(CF_3)_2$, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl.

The term "$C_1$-$C_6$-alkoxy" refers to a straight-chain or branched alkyl group having 1 to 6 carbon atoms (as defined above) which is bonded via an oxygen, at any position in the alkyl group, for example methoxy, ethoxy, n-propoxy, 1-methylethoxy, butoxy, 1-methylpropoxy, 2-methylpropoxy or 1,1-dimethylethoxy.

The term "$C_1$-$C_6$-haloalkoxy" refers to a $C_1$-$C_6$-alkoxy group as defined above, wherein some or all of the hydrogen atoms may be replaced by halogen atoms as mentioned above, for example, $OCH_2F$, $OCHF_2$, $OCF_3$, $OCH_2Ol$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $CO_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromo¬ethoxy, 4-fluorobutoxy, 4-chlorobutoxy, 4-bromobutoxy or nonafluorobutoxy.

The terms "phenyl-$C_1$-$C_4$-alkyl or heteroaryl-$C_1$-$C_4$-alkyl" refer to alkyl having 1 to 4 carbon atoms (as defined above), wherein one hydrogen atom of the alkyl radical is replaced by a phenyl or hetereoaryl radical respectively.

The term "$C_1$-$C_4$-alkoxy-$C_1$-$C_4$-alkyl" refers to alkyl having 1 to 4 carbon atoms (as defined above), wherein one hydrogen atom of the alkyl radical is replaced by a $C_1$-$C_4$-alkoxy group (as defined above). Likewise, the term "$C_1$-$C_4$-alkylthio-$C_1$-$C_4$-alkyl" refers to alkyl having 1 to 4 carbon atoms (as defined above), wherein one hydrogen atom of the alkyl radical is replaced by a $C_1$-$C_4$-alkylthio group.

The term "$C_1$-$C_6$-alkylthio" as used herein refers to straight-chain or branched alkyl groups having 1 to 6 carbon atoms (as defined above) bonded via a sulfur atom. Accordingly, the term "$C_1$-$C_6$-haloalkylthio" as used herein refers to straight-chain or branched haloalkyl group having 1 to 6 carbon atoms (as defined above) bonded through a sulfur atom, at any position in the haloalkyl group.

The term "$C_1$-$C_6$-alkylsulfinyl" refers to straight-chain or branched alkyl groups having 1 to 6 carbon atoms (as defined above) bonded through a —S(=O)— moiety, at any position in the alkyl group, for example methylsulfinyl and ethylsulfinyl, and the like. Accordingly, the term "$C_1$-$C_6$-haloalkylsulfinyl" refers to straight-chain or branched haloalkyl group having 1 to 6 carbon atoms (as defined above), bonded through a —S(=O)— moiety, at any position in the haloalkyl group.

The term "$C_1$-$C_6$-alkylsulfonyl" refers to straight-chain or branched alkyl groups having 1 to 6 carbon atoms (as defined above), bonded through a —S(=O)$_2$— moiety, at any position in the alkyl group, for example methylsulfonyl. Accordingly, the term "$C_1$-$C_6$-haloalkylsulfonyl" refers to straight-chain or branched haloalkyl group having 1 to 6 carbon atoms (as defined above), bonded through a —S(=O)$_2$— moiety, at any position in the haloalkyl group.

The term "hydroxy$C_1$-$C_4$-alkyl" refers to alkyl having 1 to 4 carbon atoms, wherein one hydrogen atom of the alkyl radical is replaced by a OH group.

The term "amino$C_1$-$C_4$-alkyl" refers to alkyl having 1 to 4 carbon atoms, wherein one hydrogen atom of the alkyl radical is replaced by a $NH_2$ group.

The term "di$C_1$-$C_6$-alkylamino" refers to an amino group, which is substituted with two residues independently selected from the group that is defined by the term $C_1$-$C_6$-alkyl.

The term "$C_1$-$C_4$-alkylamino-$C_1$-$C_4$-alkyl" refers to alkyl having 1 to 4 carbon atoms (as defined above), wherein one hydrogen atom of the alkyl radical is replaced by a $C_1$-$C_4$-alkyl-NH— group which is bound through the nitrogen. Likewise the term "di$C_1$-$C_4$-alkylamino-$C_1$-$C_4$-alkyl" refers to refers to alkyl having 1 to 4 carbon atoms (as defined above), wherein one hydrogen atom of the alkyl radical is replaced by a ($C_1$-$C_4$-alkyl)$_2$N— group which is bound through the nitrogen. The term "aminocarbonyl-$C_1$-$C_4$-alkyl" refers to alkyl having 1 to 4 carbon atoms, wherein one hydrogen atom of the alkyl radical is replaced by a —C(=O)—NH$_2$ group.

The term "$C_2$-$C_6$-alkenyl" refers to a straight-chain or branched unsaturated hydrocarbon radical having 2 to 6 carbon atoms and a double bond in any position, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

The term "$C_2$-$C_6$-alkynyl" refers to a straight-chain or branched unsaturated hydrocarbon radical having 2 to 6 carbon atoms and containing at least one triple bond, such as ethynyl, 1-propynyl, 2-propynyl (propargyl), 1-butynyl, 2-butynyl, 3-butynyl, 1-methyl-2-propynyl.

The term "$C_3$-$C_8$-cycloalkyl" refers to monocyclic saturated hydrocarbon radicals having 3 to 8 carbon ring members such as cyclopropyl ($C_3H_5$), cyclobutyl, cyclopentyl, cyclohexyl, cycloheptyl or cyclooctyl.

The term "$C_3$-$C_8$-cycloalkyloxy" refers to a cycloalkyl radical having 3 to 8 carbon atoms (as defined above), which is bonded via an oxygen.

The term "C(=O)—$C_1$-$C_4$-alkyl" refers to a radical which is attached through the carbon atom of the —C(=O)- group as indicated by the number valence of the carbon atom.

The term "aliphatic" refers to compounds or radicals composed of carbon and hydrogen and which are non-aromatic compounds. An alicyclic compound or radical is an organic compound that is both aliphatic and cyclic. They contain one or more all-carbon rings which may be either saturated or unsaturated, but do not have aromatic character.

The terms "cyclic moiety" or "cyclic group" refer to a radical which is an alicyclic ring or an aromatic ring, such as, for example, phenyl or heteroaryl.

The term "and wherein any of the aliphatic or cyclic groups are unsubstituted or substituted with 1, 2, 3, 4 or up to the maximum possible number of identical or different groups $R^{1a}$" refers to aliphatic groups, cyclic groups and groups, which contain an aliphatic and a cyclic moiety in one group, such as in, for example, phenyl-$C_1$-$C_4$-alkyl; therefore a group which contains an aliphatic and a cyclic moiety both of these moieties may be substituted or unsubstituted independently of each other.

The term "aryl" refers to aromatic monocyclic or polycyclic ring systems which may or may not include, besides carbon atoms, 1, 2, 3 or 4 heteroatoms independently selected from the group consisting of N, O and S.

The term "heteroaryl" refers to aromatic monocyclic or polycyclic ring systems including besides carbon atoms, 1, 2, 3 or 4 heteroatoms independently selected from the group consisting of N, O and S.

The term "phenyl" refers to an aromatic ring systems including six carbon atoms (commonly referred to as benzene ring). In association with the group A the term "phenyl" is to be interpreted as a benzene ring or phenylene ring, which is attached to both, the oxadiazole moiety and the —C(=S)NR$^1$R$^2$— group.

The term "3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms", is to be understood as meaning both, aromatic mono- and bicyclic heteroaromatic ring systems, and also saturated and partially unsaturated heterocycles, for example:

a 3- or 4-membered saturated heterocycle which contains 1 or 2 heteroatoms from the group consisting of N, O and S as ring members such as oxirane, aziridine, thiirane, oxetane, azetidine, thiethane, [1,2]dioxetane, [1,2]dithietane, [1,2]diazetidine;

and a 5- or 6-membered saturated or partially unsaturated heterocycle which contains 1, 2 or 3 heteroatoms from the group consisting of N, O and S as ring members such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl and also the corresponding -ylidene radicals; and a 7-membered saturated or partially unsaturated heterocycle such as tetra- and hexahydroazepinyl, such as 2,3,4,5-tetrahydro[1H]azepin-1-,-2-,-3-,-4-,-5-,-6- or -7-yl, 3,4,5,6-tetrahydro[2H]azepin-2-,-3-,-4-,-5-,-6- or -7-yl, 2,3,4,7-tetrahydro[1H]azepin-1-,-2-,-3-,-4-,-5-,-6- or -7-yl, 2,3,6,7-tetrahydro[1H]azepin-1-,-2-,-3-,-4-,-5-,-6- or -7-yl, hexahydroazepin-1-,-2-,-3- or -4-yl, tetra- and hexahydroxepinyl such as 2,3,4,5-tetrahydro[1H]oxepin-2-,-3-,-4-,-5-,-6- or -7-yl, 2,3,4,7-tetrahydro[1H]oxepin-2-,-3-,-4-,-5-,-6- or -7-yl, 2,3,6,7-tetrahydro[1H]oxepin-2-, -3-,-4-,-5-,-6- or -7-yl, hexahydroazepin-1-,-2-,-3- or -4-yl, tetra- and hexahydro-1,3-diazepinyl, tetra- and hexahydro-1,4-diazepinyl, tetra- and hexahydro-1,3-oxazepinyl, tetra- and hexahydro-1,4-oxazepinyl, tetra- and hexahydro-1,3-dioxepinyl, tetra- and hexahydro-1,4-dioxepinyl and the corresponding -ylidene radicals; and the term "5- or 6-membered heteroaryl" or the term "5- or 6-membered aromatic heterocycle" refer to aromatic ring systems including besides carbon atoms, 1, 2, 3 or 4 heteroatoms independently selected from the group consisting of N, O and S, for example, a 5-membered heteroaryl such as pyrrol-1-yl, pyrrol-2-yl, pyrrol-3-yl, thien-2-yl, thien-3-yl, furan-2-yl, furan-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-triazolyl-1-yl, 1,2,4-triazol-3-yl 1,2,4-triazol-5-yl, 1,2,4-oxadiazol-3-yl, 1,2,4-oxadiazol-5-yl and 1,2,4-thiadiazol-3-yl, 1,2,4-thiadiazol-5-yl; or a 6-membered heteroaryl, such as pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and 1,3,5-triazin-2-yl and 1,2,4-triazin-3-yl.

In respect of the variables, the embodiments of the intermediates correspond to the embodiments of the compounds I. Preference is given to those compounds I and, where applicable, also to compounds of all sub-formulae provided herein, e. g. formulae (I.1) to (I.8).

In respect of the variables, the embodiments of the intermediates correspond to the embodiments of the compounds I. Preference is given to those compounds I and, where applicable, also to compounds of all sub-formulae provided herein, e. g. formulae (I.1) to (I.8), wherein variables such as $R^1$, $R^2$, A, $R^A$, $R^a$ and $R^{1a}$ have independently of each other or more preferably in combination (any possible combination of 2 or more substituents as defined herein) the following meanings:

In one aspect of the invention A is phenyl which is unsubstituted or substituted with 1, 2, 3 or 4 identical or different groups $R^A$ as defined or preferably defined herein and wherein the group —C(=S)NR$^1$R$^2$ is attached to the phenyl ring in para-position with regard to the trifluoromethyloxadiazole group.

In one embodiment A is thiophenyl, wherein the aromatic heterocycle is unsubstituted or substituted with 1 or 2 identical or different groups $R^A$ as defined or preferably defined herein; particularly $R^A$ is chlorine, fluorine or methyl.

In one embodiment the invention relates to compounds of the formula I, or the N-oxides, or the agriculturally acceptable salts thereof, wherein the cyclic moiety A is defined as in subformulae (A.1) to (A.3),

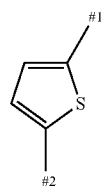
(A.1)

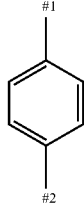
(A.2)

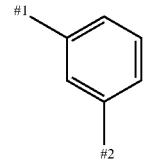
(A.3)

wherein #1 shall denote the position which is bound to the trifluoromethyloxadiazole moiety and #2 denotes the position, which is connected to the —C(=S)NR$^1$R$^2$ group of compounds of the formula I; and wherein the cyclic moiety A is unsubstituted or substituted with 1 or 2 identical or different groups $R^A$ and wherein $R^A$ is as defined or preferably defined herein. In another embodiment the cyclic moieties A as defined in any one of subformulae (A.1) to (A.3) is unsubstituted or substituted with 1 or 2 identical or different groups $R^A$; and wherein $R^A$ is chlorine, fluorine or methyl. In a preferred embodiment the cyclic moiety A as defined in any one of subformulae (A.1) to (A.3) is unsubstituted.

In a preferred embodiment of the invention $R^A$ is halogen, cyano, $C_1$-$C_6$-alkyl, $C_1$-$C_6$-alkoxy, $C_2$-$C_6$-alkenyl, $C_2$-$C_6$-alkynyl or $C_3$-$C_8$-cycloalkyl; and wherein any of the aliphatic and cyclic moieties are unsubstituted or substituted with 1, 2, 3, 4 or up to the maximum possible number of identical or different groups $R^a$ as defined or preferably defined herein.

In another preferred embodiment of the invention $R^A$ is halogen, cyano, $C_1$-$C_6$-alkyl, $C_1$-$C_6$-alkoxy, $C_2$-$C_6$-alkenyl, $C_2$-$C_6$-alkynyl or $C_3$-$C_8$-cycloalkyl; and wherein any of the the aliphatic and cyclic moieties are unsubstituted or substituted with 1, 2, 3, 4 or up to the maximum possible number of identical or different groups selected from halogen, cyano, $C_1$-$C_6$-alkyl, $C_1$-$C_6$-alkoxy and $C_3$-$C_8$-cycloalkyl; in particular fluorine.

More preferably $R^A$ is halogen, cyano, $C_1$-$C_6$-alkyl, $C_1$-$C_6$-haloalkyl, $C_1$-$C_6$-alkoxy or $C_1$-$C_6$-haloalkoxy; in particular halogen, $C_1$-$C_6$-alkyl; more particularly chlorine, fluorine, methyl. In a more preferable embodiment $R^A$ is chlorine, fluorine or methyl.

$R^a$ according to the invention is halogen, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio or $C_3$-$C_8$-cycloalkyl. In a preferred embodiment of the invention $R^a$ is halogen, cyano, $C_1$-$C_6$-alkyl, $C_1$-$C_6$-alkoxy or $C_3$-$C_8$-cycloalkyl. More preferably $R^a$ is halogen, in particular fluorine.

In one aspect of the invention $R^1$ and $R^2$ independently of each other are hydrogen, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, —C(=O)—($C_1$-$C_6$-alkyl) or —C(=O)—($C_1$-$C_6$-alkoxy); and wherein any of the above-mentioned aliphatic or cyclic groups are unsubstituted or substituted with 1, 2, 3 or up to the maximum possible number of identical or different groups $R^{1a}$ as defined or preferably defined herein.

In one aspect of the invention $R^1$ and $R^2$ independently of each other are hydrogen, $C_1$-$C_6$-alkyl, $C_2$-$C_6$-alkenyl, $C_2$-$C_6$-alkynyl, $C_3$-$C_6$-cycloalkyl or $C_3$-$C_6$-cycloalkenyl; and wherein any of the above-mentioned aliphatic or cyclic groups are unsubstituted or substituted with 1, 2, 3 or up to the maximum possible number of identical or different groups $R^{1a}$ as defined or preferably defined herein.

In a further aspect of the invention $R^1$ is hydrogen, $C_1$-$C_6$-alkyl, $C_2$-$C_6$-alkenyl or $C_2$-$C_6$-alkynyl and $R^2$ is phenyl-$C_1$-$C_4$-alkyl, heteroaryl-$C_1$-$C_4$-alkyl, phenyl or heteroaryl; and wherein the heteroaryl group is a 5- or 6-membered aromatic heterocycle wherein the ring includes besides carbon atoms 1, 2, 3 or 4 heteroatoms selected from N, O and S as ring member atoms; and wherein any of the above-mentioned aliphatic or cyclic groups are unsubstituted or substituted with 1, 2, 3 or up to the maximum possible number of identical or different groups $R^{1a}$ as defined or preferably defined herein.

In another aspect of the invention $R^1$ and $R^2$ together with the nitrogen atom to which they are bound form a saturated or partially unsaturated 3- to 6-membered heterocycle, wherein the heterocycle includes beside one nitrogen atom and one or more carbon atoms 1, 2 or 3 heteroatoms independently selected from N, O and S as ring member atoms; and wherein one or two $CH_2$ groups of the heterocycle may be replaced by one or two groups independently selected from the group of —C(=O)— and —C(=S)—; and wherein the heterocycle is unsubstituted or substituted with 1, 2, 3, 4 or up to the maximum possible number of identical or different groups $R^{1a}$ as defined or preferably defined herein.

In still another aspect of the invention $R^1$ and $R^2$ together with the nitrogen atom to which they are bound form a saturated or partially unsaturated 3- to 6-membered heterocycle, wherein the heterocycle includes beside one nitrogen atom and one or more carbon atoms one additional heteroatom selected from N, O and S as ring a member atom; and wherein the heterocycle is unsubstituted or substituted with 1, 2, 3, 4 or up to the maximum possible number of identical or different groups $R^{1a}$ as defined or preferably defined herein.

In one embodiment $R^1$ is hydrogen or methyl and $R^2$ is $C_3$-$C_6$-cycloalkyl, wherein the cycloalkyl group is unsubstituted or substituted with 1, 2, 3, 4 or up to the maximum possible number of identical or different groups $R^{1a}$ as defined or preferably defined herein.

In one embodiment $R^1$ is hydrogen or methyl and $R^2$ $C_1$-$C_6$-alkyl, $C_2$-$C_6$-alkenyl or $C_2$-$C_6$-alkynyl, wherein the aliphatic groups are unsubstituted or substituted with 1, 2, 3, 4 or up to the maximum possible number of identical or different groups $R^{1a}$ as defined or preferably defined herein.

In another embodiment $R^1$ is hydrogen or methyl and $R^2$ is methyl, ethyl, n-propyl, isopropyl, n-butyl, isobutyl or cyclopropyl; and wherein any of the aliphatic or cyclic groups are unsubstituted or substituted with 1, 2, 3, 4 or 5 or up to the maximum possible number of identical or different groups $R^{1a}$ as defined or preferably defined herein.

In yet another embodiment $R^1$ is hydrogen or methyl and $R^2$ is phenyl-$C_1$-$C_4$-alkyl, heteroaryl-$C_1$-$C_4$-alkyl, $C_3$-$C_6$-cycloalkyl-$C_1$-$C_4$-alkyl; and wherein any of the aliphatic or cyclic groups are unsubstituted or substituted with 1, 2, 3, 4 or 5 up to the maximum possible number of identical or different groups $R^{1a}$ as defined or preferably defined herein.

In one embodiment $R^1$ is hydrogen or methyl and $R^2$ is heteroaryl-$C_1$-$C_4$-alkyl, wherein any of the aliphatic or cyclic groups are unsubstituted or substituted with 1, 2, 3 or up to the maximum possible number of identical or different groups $R^{1a}$ as defined or preferably defined herein. In one embodiment $R^1$ is hydrogen or methyl and $R^2$ is phenyl, wherein the phenyl group is unsubstituted or substituted with 1, 2, 3, 4 or up to the maximum possible number of identical or different groups $R^{1a}$ as defined or preferably defined herein.

In a preferred embodiment of the invention $R^{1a}$ is halogen, cyano, $C_1$-$C_6$-alkyl, $C_1$-$C_6$-haloalkyl, $C_1$-$C_6$-alkoxy, $C_1$-$C_6$-haloalkoxy or $C_3$-$C_8$-cycloalkyl. In another preferred aspect of the invention $R^{1a}$ is halogen, cyano, $C_1$-$C_6$-alkyl, $C_1$-$C_6$-haloalkyl, $C_1$-$C_6$-alkoxy or $C_1$-$C_6$-haloalkoxy. In a more preferred aspect of the invention $R^{1a}$ is halogen or cyano; in particular halogen; most particularly fluorine.

In a further embodiment the invention relates to compounds (I.1) of formula I, or the N-oxides, or the agriculturally acceptable salts thereof, wherein:
A is selected from the group consisting of subformulae (A.1) to (A.3), which are unsubstituted or substituted with 1 or 2 identical or different groups $R^A$; wherein
$R^A$ is halogen, cyano, $C_1$-$C_6$-alkyl, $C_1$-$C_6$-alkoxy, $C_1$-$C_6$-alkylsulfonyl, $C_2$-$C_6$-alkenyl, $C_2$-$C_6$-alkynyl, $C_3$-$C_8$-cycloalkyl or $C_3$-$C_8$-cycloalkoxy; and wherein the aliphatic and cyclic moieties are unsubstituted or substituted with 1, 2, 3 or 4 identical or different groups $R^a$; wherein
$R^a$ is halogen, cyano, $C_1$-$C_6$-alkyl, $C_1$-$C_6$-alkoxy or $C_3$-$C_8$-cycloalkyl;
$R^1$ is hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, C(=O)—($C_1$-$C_6$-alkyl) or C(=O)—($C_1$-$C_6$-alkoxy);
$R^2$ is phenyl, a 5- or 6-membered aromatic heterocycle, phenyl-$C_1$-$C_4$-alkyl or heteroaryl-$C_1$-$C_4$-alkyl; wherein the ring member atoms of the aromatic heterocycle include besides carbon atoms 1, 2, 3 or 4 heteroatoms selected from N, O and S as ring member atoms; and wherein any of the cyclic groups are unsubstituted or substituted with 1, 2, 3 or 4 identical or different groups selected from the group consisting of halogen, cyano, $C_1$-$C_6$-alkyl, $C_1$-$C_6$-haloalkyl, $C_1$-$C_6$-alkoxy and $C_1$-$C_6$-haloalkoxy.

In another embodiment the invention relates to compounds (I.1), wherein A is (A.1). In a further embodiment the invention relates to compounds (I.1), wherein A is (A.1), and wherein A is substituted with 1 group $R^A$ as defined or preferably defined herein. In yet another embodiment the invention relates to compounds (I.1), wherein A is (A.1), and wherein A is unsubstituted. In another embodiment the invention relates to compounds (I.1), wherein A is (A.2). In a further embodiment the invention relates to compounds (I.1), wherein A is (A.2), and wherein A is substituted with 1 group $R^A$ as defined or preferably defined herein. In yet another embodiment the invention relates to compounds (I.1), wherein A is (A.2), and wherein A is unsubstituted.

In a further embodiment the invention relates to compounds (I.2) of formula I, or the N-oxides, or the agriculturally acceptable salts thereof, wherein:
A is selected from the group consisting of subformulae (A.1) to (A.3), which are unsubstituted or substituted with 1 or 2 identical or different groups $R^A$; wherein
$R^A$ is halogen, cyano, $C_1$-$C_6$-alkyl, $C_1$-$C_6$-alkoxy, $C_1$-$C_6$-alkylsulfonyl, $C_2$-$C_6$-alkenyl, $C_2$-$C_6$-alkynyl, $C_3$-$C_8$-cycloalkyl or $C_3$-$C_8$-cycloalkoxy; and wherein the aliphatic and cyclic moieties are unsubstituted or substituted with 1, 2, 3 or 4 identical or different groups $R^a$; wherein $R^a$ is halogen, cyano, $C_1$-$C_6$-alkyl, $C_1$-$C_6$-alkoxy or $C_3$-$C_8$-cycloalkyl;

$R^1$ is hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, C(=O)—($C_1$-$C_6$-alkyl) or C(=O)—($C_1$-$C_6$-alkoxy);

$R^2$ is phenyl, which is unsubstituted or substituted with 1, 2, 3 or 4 identical or different groups selected from the group consisting of halogen, cyano, $C_1$-$C_6$-alkyl, $C_1$-$C_6$-haloalkyl, $C_1$-$C_6$-alkoxy and $C_1$-$C_6$-haloalkoxy.

In another embodiment the invention relates to compounds (I.2), wherein A is (A.1). In a further embodiment the invention relates to compounds (I.2), wherein A is (A.1), and wherein A is substituted with 1 group $R^A$ as defined or preferably defined herein. In yet another embodiment the invention relates to compounds (I.2), wherein A is (A.1), and wherein A is unsubstituted. In another embodiment the invention relates to compounds (I.2), wherein A is (A.2). In a further embodiment the invention relates to compounds (I.2), wherein A is (A.2), and wherein A is substituted with 1 group $R^A$ as defined or preferably defined herein. In yet another embodiment the invention relates to compounds (I.2), wherein A is (A.2), and wherein A is unsubstituted.

In yet another embodiment the invention relates to compounds (I.3) of formula I, or the N-oxides, or the agriculturally acceptable salts thereof, wherein:

A is selected from the group consisting of subformulae (A.1) to (A.3), which are unsubstituted or substituted with 1 or 2 identical or different groups $R^A$; wherein
$R^A$ is halogen, $C_1$-$C_6$-alkyl, $C_1$-$C_6$-haloalkyl, $C_1$-$C_6$-alkoxy or $C_1$-$C_6$-haloalkoxy;

$R^1$ is hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkenyl, C(=O)—($C_1$-$C_6$-alkyl) or C(=O)—($C_1$-$C_6$-alkoxy);

$R^2$ is phenyl, which is unsubstituted or substituted with 1, 2, 3 or 4 identical or different groups selected from the group consisting of halogen, cyano, $C_1$-$C_6$-alkyl, $C_1$-$C_6$-haloalkyl, $C_1$-$C_6$-alkoxy and $C_1$-$C_6$-haloalkoxy.

In another embodiment the invention relates to compounds (I.3), wherein A is (A.1). In a further embodiment the invention relates to compounds (I.3), wherein A is (A.1), and wherein A is substituted with 1 group $R^A$ as defined or preferably defined herein. In yet another embodiment the invention relates to compounds (I.3), wherein A is (A.1), and wherein A is unsubstituted. In another embodiment the invention relates to compounds (I.3), wherein A is (A.2). In a further embodiment the invention relates to compounds (I.3), wherein A is (A.2), and wherein A is substituted with 1 group $R^A$ as defined or preferably defined herein. In yet another embodiment the invention relates to compounds (I.3), wherein A is (A.2), and wherein A is unsubstituted.

In yet another embodiment the invention relates to compounds (I.4) of formula I, or the N-oxides, or the agriculturally acceptable salts thereof, wherein:

A is selected from the group consisting of subformulae (A.1) to (A.3), which are unsubstituted or substituted with 1 or 2 identical or different groups $R^A$; wherein
$R^A$ is halogen, cyano, $C_1$-$C_6$-alkyl, $C_1$-$C_6$-haloalkyl, $C_1$-$C_6$-alkoxy or $C_1$-$C_6$-haloalkoxy;

$R^1$ is hydrogen, $C_1$-$C_6$-alkyl, $C_2$-$C_6$-alkenyl or $C_2$-$C_6$-alkynyl;

$R^2$ is phenyl, which is unsubstituted or substituted with 1, 2, 3 or 4 identical or different groups selected from the group consisting of halogen, cyano, $C_1$-$C_6$-alkyl, $C_1$-$C_6$-haloalkyl, $C_1$-$C_6$-alkoxy and $C_1$-$C_6$-haloalkoxy.

In another embodiment the invention relates to compounds (I.4), wherein A is (A.1). In a further embodiment the invention relates to compounds (I.4), wherein A is (A.1), and wherein A is substituted with 1 group $R^A$ as defined or preferably defined herein. In yet another embodiment the invention relates to compounds (I.4), wherein A is (A.1), and wherein A is unsubstituted. In another embodiment the invention relates to compounds (I.4), wherein A is (A.2). In a further embodiment the invention relates to compounds (I.4), wherein A is (A.2), and wherein A is substituted with 1 group $R^A$ as defined or preferably defined herein. In yet another embodiment the invention relates to compounds (I.4), wherein A is (A.2), and wherein A is unsubstituted.

In still another embodiment the invention relates to compounds (I.5) of formula I, or the N-oxides, or the agriculturally acceptable salts thereof, wherein:

A is selected from the group consisting of subformulae (A.1) to (A.3), which are unsubstituted or substituted with 1 or 2 identical or different groups $R^A$; wherein
$R^A$ is halogen, cyano, $C_1$-$C_6$-alkyl, $C_1$-$C_6$-alkoxy, $C_1$-$C_6$-alkylsulfonyl, $C_2$-$C_6$-alkenyl, $C_2$-$C_6$-alkynyl, $C_3$-$C_8$-cycloalkyl or $C_3$-$C_8$-cycloalkoxy; and wherein the aliphatic and cyclic moieties are unsubstituted or substituted with 1, 2, 3 or 4 identical or different groups $R^a$; wherein
$R^a$ is halogen, cyano, $C_1$-$C_6$-alkyl, $C_1$-$C_6$-alkoxy or $C_3$-$C_8$-cycloalkyl;

$R^1$ and $R^2$ independently of each other are hydrogen, $C_1$-$C_6$-alkyl, $C_2$-$C_6$-alkenyl, $C_2$-$C_6$-alkynyl, $C_3$-$C_8$-cycloalkyl or $C_3$-$C_8$-cycloalkenyl; in particular methyl, ethyl, n-propyl, isopropyl, n-butyl, isobutyl or cyclopropyl; and wherein the aliphatic and the cyclic groups are unsubstituted or substituted with 1, 2, 3, 4 or up to the maximum possible number of identical or different groups $R^{1a}$ as defined or preferably defined herein.

In another embodiment the invention relates to compounds (I.5), wherein A is (A.1). In a further embodiment the invention relates to compounds (I.5), wherein A is (A.1), and wherein A is substituted with 1 group $R^A$ as defined or preferably defined herein. In yet another embodiment the invention relates to compounds (I.5), wherein A is (A.1), and wherein A is unsubstituted. In another embodiment the invention relates to compounds (I.5), wherein A is (A.2). In a further embodiment the invention relates to compounds (I.5), wherein A is (A.2), and wherein A is substituted with 1 group $R^A$ as defined or preferably defined herein. In yet another embodiment the invention relates to compounds (I.5), wherein A is (A.2), and wherein A is unsubstituted.

In a further embodiment the invention relates to compounds (I.6) of formula I, or the N-oxides, or the agriculturally acceptable salts thereof, wherein:

A is selected from the group consisting of subformulae (A.1) to (A.3), which are unsubstituted or substituted with 1 or 2 identical or different groups $R^A$; wherein
$R^A$ is halogen, cyano, $C_1$-$C_6$-alkyl, $C_1$-$C_6$-haloalkyl, $C_1$-$C_6$-alkoxy or $C_1$-$C_6$-haloalkoxy;

$R^1$ and $R^2$ independently of each other are hydrogen, $C_1$-$C_6$-alkyl, $C_2$-$C_6$-alkenyl, $C_2$-$C_6$-alkynyl, $C_3$-$C_8$-cycloalkyl or $C_3$-$C_8$-cycloalkenyl; in particular hydrogen, methyl, ethyl, n-propyl, isopropyl, n-butyl, isobutyl or cyclopropyl.

In another embodiment the invention relates to compounds (I.6), wherein A is (A.1). In a further embodiment the invention relates to compounds (I.6), wherein A is (A.1), and wherein A is substituted with 1 group $R^A$ as defined or preferably defined herein. In yet another embodiment the invention relates to compounds (I.6), wherein A is (A.1), and wherein A is unsubstituted. In another embodiment the invention relates to compounds (I.6), wherein A is (A.2). In a further embodiment the invention relates to compounds (I.6), wherein A is (A.2), and wherein A is substituted with 1 group $R^A$ as defined or preferably defined herein. In yet another embodiment the invention relates to compounds (I.6), wherein A is (A.2), and wherein A is unsubstituted.

In a further embodiment the invention relates to compounds (I.7) of formula I, or the N-oxides, or the agriculturally acceptable salts thereof, wherein:

A is selected from the group consisting of subformulae (A.1) to (A.3), which are unsubstituted or substituted with 1 or 2 identical or different groups $R^A$; wherein
  $R^A$ is halogen, cyano, $C_1$-$C_6$-alkyl, $C_1$-$C_6$-alkoxy, $C_1$-$C_6$-alkylsulfonyl, $C_2$-$C_6$-alkenyl, $C_2$-$C_6$-alkynyl, $C_3$-$C_8$-cycloalkyl or $C_3$-$C_8$-cycloalkoxy; and wherein the aliphatic and cyclic moieties are unsubstituted or substituted with 1, 2, 3 or 4 identical or different groups $R^a$; wherein
    $R^a$ is halogen, cyano, $C_1$-$C_6$-alkyl, $C_1$-$C_6$-alkoxy or $C_3$-$C_8$-cycloalkyl;
$R^1$ and $R^2$ together with the nitrogen atom to which they are bound form a saturated or partially unsaturated 3- to 6-membered heterocycle, wherein the heterocycle includes beside one nitrogen atom and carbon atoms no further heteroatoms or 1, 2 or 3 heteroatoms independently selected from N, O and S as ring member atoms; and wherein one or two $CH_2$ groups of the carbo- or heterocycle may be replaced by one or two groups independently selected from the group of C(=O) and C(=S); and wherein the heterocycle is unsubstituted or substituted with 1, 2, 3, 4 or up to the maximum possible number of identical or different groups $R^{1a}$ as defined or preferably defined herein.

In another embodiment the invention relates to compounds (I.7), wherein A is (A.1). In a further embodiment the invention relates to compounds (I.7), wherein A is (A.1), and wherein A is substituted with 1 group $R^A$ as defined or preferably defined herein. In yet another embodiment the invention relates to compounds (I.7), wherein A is (A.1), and wherein A is unsubstituted. In another embodiment the invention relates to compounds (I.7), wherein A is (A.2). In a further embodiment the invention relates to compounds (I.7), wherein A is (A.2), and wherein A is substituted with 1 group $R^A$ as defined or preferably defined herein. In yet another embodiment the invention relates to compounds (I.7), wherein A is (A.2), and wherein A is unsubstituted.

In a further embodiment the invention relates to compounds (I.8) of formula I, or the N-oxides, or the agriculturally acceptable salts thereof, wherein:

A is selected from the group consisting of subformulae (A.1) to (A.3), which are unsubstituted or substituted with 1 or 2 identical or different groups $R^A$; wherein
  $R^A$ is halogen, cyano, $C_1$-$C_6$-alkyl, $C_1$-$C_6$-haloalkyl, $C_1$-$C_6$-alkoxy or $C_1$-$C_6$-haloalkoxy;
$R^1$ and $R^2$ together with the nitrogen atom to which they are bound form a saturated or partially unsaturated 3- to 6-membered heterocycle, wherein the heterocycle includes beside one nitrogen atom and carbon atoms no further heteroatoms or 1, 2 or 3 heteroatoms independently selected from N, O and S as ring member atoms; and wherein the heterocycle is unsubstituted or substituted with 1, 2, 3 or 4 identical or different groups selected from halogen, cyano, $C_1$-$C_6$-alkyl, $C_1$-$C_6$-haloalkyl, $C_1$-$C_6$-alkoxy and $C_1$-$C_6$-haloalkoxy.

In another embodiment the invention relates to compounds (I.8), wherein A is (A.1). In a further embodiment the invention relates to compounds (I.8), wherein A is (A.1), and wherein A is substituted with 1 group $R^A$ as defined or preferably defined herein. In yet another embodiment the invention relates to compounds (I.8), wherein A is (A.1), and wherein A is unsubstituted. In another embodiment the invention relates to compounds (I.8), wherein A is (A.2). In a further embodiment the invention relates to compounds (I.8), wherein A is (A.2), and wherein A is substituted with 1 group $R^A$ as defined or preferably defined herein. In yet another embodiment the invention relates to compounds (I.8), wherein A is (A.2), and wherein A is unsubstituted.

According to one embodiment, the present invention relates to compounds of the formula I.A

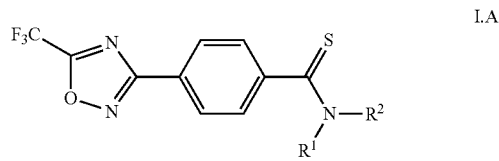

I.A or to the use of the compounds of the formula I.A for controlling phytopathogenic fungi, wherein $R^1$ and $R^2$ are as defined or preferably defined herein for formula I.

According to one embodiment, the present invention relates to compounds of the formula I.B

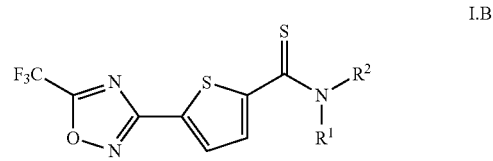

I.B or to the use of the compounds of the formula I.B for controlling phytopathogenic fungi, wherein $R^1$ and $R^2$ are as defined or preferably defined herein for formula I.

Preference is given to the compounds I and their use according to the invention which are compiled in Tables 1 and 2 below. The combinations of groups $R^1$ and $R^2$ mentioned in table A and referenced in table 1 and table 2 are furthermore per se, independently of the combination in which they are mentioned, a particularly preferred aspect of the substituent in question.

Table 1

Compounds of the formula I.A, in which $R^1$ and $R^2$ for each individual compound corresponds in each case to one line A-1 to A-473 of Table A (I.A.A-1 to I.A.A-473).

Table 2

Compounds of the formula I.B, in which $R^1$ and $R^2$ for each individual compound corresponds in each case to one line A-1 to A-473 of Table A (I.B.A-1 to I.B.A-473).

TABLE A

| No | $R^1$ | $R^2$ |
|---|---|---|
| A-1 | H | H |
| A-2 | H | $CH_3$ |
| A-3 | H | $CH_2CH_3$ |
| A-4 | H | $CH_2CH_2CH_3$ |
| A-5 | H | $CH(CH_3)_2$ |
| A-6 | H | $CH_2CH_2CH_2CH_3$ |
| A-7 | H | $CH(CH_3)CH_2CH_3$ |
| A-8 | H | $CH_2CH(CH_3)CH_3$ |
| A-9 | H | $C(CH_3)_3$ |
| A-10 | H | allyl |
| A-11 | H | propargyl |
| A-12 | H | $CH_2CN$ |

TABLE A-continued

| No | R¹ | R² |
|---|---|---|
| A-13 | H | cyclopropyl |
| A-14 | H | 1-methylcyclopropyl |
| A-15 | H | 1-trifluormethyl-cyclopropyl |
| A-16 | H | 1-fluorocyclopropyl |
| A-17 | H | 1-cyclopropylcyclopropyl |
| A-18 | H | 1-cyanocyclopropyl |
| A-19 | H | 2-methylcyclopropyl |
| A-20 | H | 2-ethylcyclopropyl |
| A-21 | H | 2-trifluoromethyl-cyclopropyl |
| A-22 | H | 2-fluorocyclopropyl |
| A-23 | H | 2-cyclopropylcyclopropyl |
| A-24 | H | 1-cyanocyclopropyl |
| A-25 | H | 2,2-difluorcyclopropyl |
| A-26 | H | 2,2-difluor-1-methyl-cyclopropyl |
| A-27 | H | cylopentyl |
| A-28 | H | cyclohexyl |
| A-29 | H | phenyl |
| A-30 | H | 2-pyridyl |
| A-31 | H | 3-pyridyl |
| A-32 | H | 4-pyridyl |
| A-33 | H | 2-F-phenyl |
| A-34 | H | 3-F-phenyl |
| A-35 | H | 4-F-phenyl |
| A-36 | H | 2-Cl-phenyl |
| A-37 | H | 3-Cl-phenyl |
| A-38 | H | 4-Cl-phenyl |
| A-39 | H | 2-methyl-phenyl |
| A-40 | H | 3-methyl-phenyl |
| A-41 | H | 4-methyl-phenyl |
| A-42 | H | 2-ethyl-phenyl |
| A-43 | H | 3-ethyl-phenyl |
| A-44 | H | 4-ethyl-phenyl |
| A-45 | H | 2-isopropyl-phenyl |
| A-46 | H | 3-isopropyl-phenyl |
| A-47 | H | 4-isopropyl-phenyl |
| A-48 | H | 2-(2,2,2-trifluoroethyl)-phenyl |
| A-49 | H | 3-(2,2,2-trifluoroethyl)-phenyl |
| A-50 | H | 4-(2,2,2-trifluoroethyl)-phenyl |
| A-51 | H | 2-trifluoromethyl-phenyl |
| A-52 | H | 3-trifluoromethyl-phenyl |
| A-53 | H | 4-trifluoromethyl-phenyl |
| A-54 | H | 2-methoxy-phenyl |
| A-55 | H | 3-methoxy-phenyl |
| A-56 | H | 4-methoxy-phenyl |
| A-57 | H | 2-trifluoromethoxy-phenyl |
| A-58 | H | 3-trifluoromethoxy-phenyl |
| A-59 | H | 4-trifluoromethoxy-phenyl |
| A-60 | H | 2-difluoromethoxy-phenyl |
| A-61 | H | 3-difluoromethoxy-phenyl |
| A-62 | H | 4-difluoromethoxy-phenyl |
| A-63 | H | 2-(2,2,2-trifluoroethoxy)-phenyl |
| A-64 | H | 3-(2,2,2-trifluoroethoxy)-phenyl |
| A-65 | H | 4-(2,2,2-trifluoroethoxy)-phenyl |
| A-66 | H | 2-cyano-phenyl |
| A-67 | H | 3-cyano-phenyl |
| A-68 | H | 4-cyano-phenyl |
| A-69 | H | 2,3-difluoro-phenyl |
| A-70 | H | 2,4-difluoro-phenyl |
| A-71 | H | 2,5-difluoro-phenyl |
| A-72 | H | 2,6-difluoro-phenyl |
| A-73 | H | 2,3-dichloro-phenyl |
| A-74 | H | 2,4-dichloro-phenyl |
| A-75 | H | 2,5-dichloro-phenyl |
| A-76 | H | 2,6-dichloro-phenyl |
| A-77 | H | 2-F-3-Cl-phenyl |
| A-78 | H | 2-F-4-Cl-phenyl |
| A-79 | H | 2-F-5-Cl-phenyl |
| A-80 | H | 2-F-6-Cl-phenyl |
| A-81 | H | 3-F-4-Cl-phenyl |
| A-82 | H | 3-F-5-Cl-phenyl |
| A-83 | H | 2-Cl-3-F-phenyl |
| A-84 | H | 2-Cl-4-F-phenyl |
| A-85 | H | 2-Cl-5-F-phenyl |
| A-86 | H | 3-Cl-4-F-phenyl |
| A-87 | H | 2-F-3-methyl-phenyl |
| A-88 | H | 2-F-4-methyl-phenyl |
| A-89 | H | 2-F-5-methyl-phenyl |
| A-90 | H | 2-F-6-methyl-phenyl |
| A-91 | H | 3-F-4-methyl-phenyl |
| A-92 | H | 3-F-5-methyl-phenyl |
| A-93 | H | 2-methyl-3-F-phenyl |
| A-94 | H | 2-methyl-4-F-phenyl |
| A-95 | H | 2-methyl-5-F-phenyl |
| A-96 | H | 3-methyl-4-F-phenyl |
| A-97 | H | 2-F-3-$CF_3$-phenyl |
| A-98 | H | 2-F-4-$CF_3$-phenyl |
| A-99 | H | 2-F-5-$CF_3$-phenyl |
| A-100 | H | 2-F-6-$CF_3$-phenyl |
| A-101 | H | 3-F-4-$CF_3$-phenyl |
| A-102 | H | 3-F-5-$CF_3$-phenyl |
| A-103 | H | 2-$CF_3$-3-F-phenyl |
| A-104 | H | 2-$CF_3$-4-F-phenyl |
| A-105 | H | 2-$CF_3$-5-F-phenyl |
| A-106 | H | 3-$CF_3$-4-F-phenyl |
| A-107 | H | 2-F-3-OMe-phenyl |
| A-108 | H | 2-F-4-OMe-phenyl |
| A-109 | H | 2-F-5-OMe-phenyl |
| A-110 | H | 2-F-6-OMe-phenyl |
| A-111 | H | 3-F-4-OMe-phenyl |
| A-112 | H | 3-F-5-OMe-phenyl |
| A-113 | H | 2-OMe-3-F-phenyl |
| A-114 | H | 2-OMe-4-F-phenyl |
| A-115 | H | 2-OMe-5-F-phenyl |
| A-116 | H | 3-OMe-4-F-phenyl |
| A-117 | H | 2-F-3-$OCHF_2$-phenyl |
| A-118 | H | 2-F-4-$OCHF_2$-phenyl |
| A-119 | H | 2-F-5-$OCHF_2$-phenyl |
| A-120 | H | 2-F-6-$OCHF_2$-phenyl |
| A-121 | H | 3-F-4-$OCHF_2$-phenyl |
| A-122 | H | 3-F-5-$OCHF_2$-phenyl |
| A-123 | H | 2-$OCHF_2$-3-F-phenyl |
| A-124 | H | 2-$OCHF_2$-4-F-phenyl |
| A-125 | H | 2-$OCHF_2$-5-F-phenyl |
| A-126 | H | 3-$OCHF_2$-4-F-phenyl |
| A-127 | H | 2-F-3-CN-phenyl |
| A-128 | H | 2-F-4-CN-phenyl |
| A-129 | H | 2-F-5-CN-phenyl |
| A-130 | H | 2-F-6-CN-phenyl |
| A-131 | H | 3-F-4-CN-phenyl |
| A-132 | H | 3-F-5-CN-phenyl |
| A-133 | H | 2-CN-3-F-phenyl |
| A-134 | H | 2-CN-4-F-phenyl |
| A-135 | H | 2-CN-5-F-phenyl |
| A-136 | H | 3-CN-4-F-phenyl |
| A-137 | H | 2-Cl-3-methyl-phenyl |
| A-138 | H | 2-Cl-4-methyl-phenyl |
| A-139 | H | 2-Cl-5-methyl-phenyl |
| A-140 | H | 2-Cl-6-methyl-phenyl |
| A-141 | H | 3-Cl-4-methyl-phenyl |
| A-142 | H | 3-Cl-5-methyl-phenyl |
| A-143 | H | 2-methyl-3-Cl-phenyl |
| A-144 | H | 2-methyl-4-Cl-phenyl |
| A-145 | H | 2-methyl-5-Cl-phenyl |
| A-146 | H | 3-methyl-4-Cl-phenyl |
| A-147 | H | 2-Cl-3-$CF_3$-phenyl |
| A-148 | H | 2-Cl-4-$CF_3$-phenyl |
| A-149 | H | 2-Cl-5-$CF_3$-phenyl |
| A-150 | H | 2-Cl-6-$CF_3$-phenyl |
| A-151 | H | 3-Cl-4-$CF_3$-phenyl |
| A-152 | H | 3-Cl-5-$CF_3$-phenyl |
| A-153 | H | 2-$CF_3$-3-Cl-phenyl |
| A-154 | H | 2-$CF_3$-4-Cl-phenyl |
| A-155 | H | 2-$CF_3$-5-Cl-phenyl |
| A-156 | H | 3-$CF_3$-4-Cl-phenyl |
| A-157 | H | 2-Cl-3-OMe-phenyl |
| A-158 | H | 2-Cl-4-OMe-phenyl |
| A-159 | H | 2-Cl-5-OMe-phenyl |
| A-160 | H | 2-Cl-6-OMe-phenyl |
| A-161 | H | 3-Cl-4-OMe-phenyl |
| A-162 | H | 3-Cl-5-OMe-phenyl |
| A-163 | H | 2-OMe-3-Cl-phenyl |
| A-164 | H | 2-OMe-4-Cl-phenyl |
| A-165 | H | 2-OMe-5-Cl-phenyl |
| A-166 | H | 3-OMe-4-Cl-phenyl |
| A-167 | H | 2-Cl-3-$OCHF_2$-phenyl |
| A-168 | H | 2-Cl-4-$OCHF_2$-phenyl |

TABLE A-continued

| No | R¹ | R² |
|---|---|---|
| A-169 | H | 2-Cl-5-OCHF$_2$-phenyl |
| A-170 | H | 2-Cl-6-OCHF$_2$-phenyl |
| A-171 | H | 3-Cl-4-OCHF$_2$-phenyl |
| A-172 | H | 3-Cl-5-OCHF$_2$-phenyl |
| A-173 | H | 2-OCHF$_2$-3-Cl-phenyl |
| A-174 | H | 2-OCHF$_2$-4-Cl-phenyl |
| A-175 | H | 2-OCHF$_2$-5-Cl-phenyl |
| A-176 | H | 3-OCHF$_2$-4-Cl-phenyl |
| A-177 | H | 2-Cl-3-CN-phenyl |
| A-178 | H | 2-Cl-4-CN-phenyl |
| A-179 | H | 2-Cl-5-CN-phenyl |
| A-180 | H | 2-Cl-6-CN-phenyl |
| A-181 | H | 3-Cl-4-CN-phenyl |
| A-182 | H | 3-Cl-5-CN-phenyl |
| A-183 | H | 2-CN-3-Cl-phenyl |
| A-184 | H | 2-CN-4-Cl-phenyl |
| A-185 | H | 2-CN-5-Cl-phenyl |
| A-186 | H | 3-CN-4-Cl-phenyl |
| A-187 | H | CH$_2$-cyclopropyl |
| A-188 | H | CH$_2$-cyclopentyl |
| A-189 | H | CH$_2$-cyclohexyl |
| A-190 | H | CH$_2$-(4-quinolinyl) |
| A-191 | H | CH$_2$-(2-pyridyl) |
| A-192 | H | CH$_2$-(3-pyridyl) |
| A-193 | H | CH$_2$-(4-pyridyl) |
| A-194 | H | CH$_2$-(2-thienyl) |
| A-195 | H | CH$_2$-(3-thienyl) |
| A-196 | H | CH$_2$-(N-methyl-3-pyrazolyl) |
| A-197 | H | CH$_2$-(N-methyl-4-pyrazolyl) |
| A-198 | H | CH$_2$-(1-pyrazolyl) |
| A-199 | H | CH$_2$-(2-oxazolyl) |
| A-200 | H | CH$_2$-(4-oxazolyl) |
| A-201 | H | CH$_2$-(5-oxazolyl) |
| A-202 | H | CH$_2$-(2-(1,3,4-oxadiazolyl)) |
| A-203 | H | CH$_2$-(2-furyl) |
| A-204 | H | CH$_2$-(3-furyl) |
| A-205 | H | 3-hydroxypropyl |
| A-206 | H | CH$_2$-(N-methyl-3-pyrrolidinyl) |
| A-207 | H | 3-dimethylaminopropyl |
| A-208 | H | 2-dimethylaminoethyl |
| A-209 | H | 3-pyrrolidinyl |
| A-210 | H | benzyl |
| A-211 | H | (2-F-phenyl)methyl |
| A-212 | H | (3-F-phenyl)methyl |
| A-213 | H | (4-F-phenyl)methyl |
| A-214 | H | (2-Cl-phenyl)methyl |
| A-215 | H | (3-Cl-phenyl)methyl |
| A-216 | H | (4-Cl-phenyl)methyl |
| A-217 | H | (2-methyl-phenyl)methyl |
| A-218 | H | (3-methyl-phenyl)methyl |
| A-219 | H | (4-methyl-phenyl)methyl |
| A-220 | H | (2-methoxy-phenyl)methyl |
| A-221 | H | (3-methoxy-phenyl)methyl |
| A-222 | H | (4-methoxy-phenyl)methyl |
| A-223 | H | (2-cyano-phenyl)methyl |
| A-224 | H | (3-cyano-phenyl)methyl |
| A-225 | H | (4-cyano-phenyl)methyl |
| A-226 | H | (2,3-difluoro-phenyl)methyl |
| A-227 | H | (2,4-difluoro-phenyl)methyl |
| A-228 | H | (2,5-difluoro-phenyl)methyl |
| A-229 | H | (2,6-difluoro-phenyl)methyl |
| A-230 | H | (2,3-dichloro-phenyl)methyl |
| A-231 | H | (2,4-dichloro-phenyl)methyl |
| A-232 | H | (2,5-dichloro-phenyl)methyl |
| A-233 | H | (2,6-dichloro-phenyl)methyl |
| A-234 | | R¹ and R² together with the nitrogen to which they are bound form a aziridinyl |
| A-235 | | R¹ and R² together with the nitrogen to which they are bound form a azetidinyl |
| A-236 | | R¹ and R² together with the nitrogen to which they are bound form a 1-pyrrolidinyl |
| A-237 | | R¹ and R² together with the nitrogen to which they are bound form a 1-piperidine |
| A-238 | | R¹ and R² together with the nitrogen to which they are bound form a 1-piperazinyl |
| A-239 | | R¹ and R² together with the nitrogen to which they are bound form a 1-methyl-4-piperazinyl |
| A-240 | | R¹ and R² together with the nitrogen to which they are bound form a 4-morpholinyl |
| A-241 | CH$_3$ | H |
| A-242 | CH$_3$ | CH$_3$ |
| A-243 | CH$_3$ | CH$_2$CH$_3$ |
| A-244 | CH$_3$ | CH$_2$CH$_2$CH$_3$ |
| A-245 | CH$_3$ | CH(CH$_3$)$_2$ |
| A-246 | CH$_3$ | CH$_2$CH$_2$CH$_2$CH$_3$ |
| A-247 | CH$_3$ | CH(CH$_3$)CH$_2$CH$_3$ |
| A-248 | CH$_3$ | CH$_2$CH(CH$_3$)CH$_3$ |
| A-249 | CH$_3$ | C(CH$_3$)$_3$ |
| A-250 | CH$_3$ | allyl |
| A-251 | CH$_3$ | propargyl |
| A-252 | CH$_3$ | CH$_2$CN |
| A-253 | CH$_3$ | cyclopropyl |
| A-254 | CH$_3$ | 1-methylcyclopropyl |
| A-255 | CH$_3$ | 1-trifluormethyl-cyclopropyl |
| A-256 | CH$_3$ | 1-fluorocyclopropyl |
| A-257 | CH$_3$ | 1-cyclopropylcyclopropyl |
| A-258 | CH$_3$ | 1-cyanocyclopropyl |
| A-259 | CH$_3$ | 2-methylcyclopropyl |
| A-260 | CH$_3$ | 2-ethylcyclopropyl |
| A-261 | CH$_3$ | 2-trifluoromethyl-cyclopropyl |
| A-262 | CH$_3$ | 2-fluorocyclopropyl |
| A-263 | CH$_3$ | 2-cyclopropylcyclopropyl |
| A-264 | CH$_3$ | 1-cyanocyclopropyl |
| A-265 | CH$_3$ | 2,2-difluorcyclopropyl |
| A-266 | CH$_3$ | 2,2-difluor-1-methyl-cyclopropyl |
| A-267 | CH$_3$ | cylopentyl |
| A-268 | CH$_3$ | cyclohexyl |
| A-269 | CH$_3$ | phenyl |
| A-270 | CH$_3$ | 2-pyridyl |
| A-271 | CH$_3$ | 3-pyridyl |
| A-272 | CH$_3$ | 4-pyridyl |
| A-273 | CH$_3$ | 2-F-phenyl |
| A-274 | CH$_3$ | 3-F-phenyl |
| A-275 | CH$_3$ | 4-F-phenyl |
| A-276 | CH$_3$ | 2-Cl-phenyl |
| A-277 | CH$_3$ | 3-Cl-phenyl |
| A-278 | CH$_3$ | 4-Cl-phenyl |
| A-279 | CH$_3$ | 2-methyl-phenyl |
| A-280 | CH$_3$ | 3-methyl-phenyl |
| A-281 | CH$_3$ | 4-methyl-phenyl |
| A-282 | CH$_3$ | 2-ethyl-phenyl |
| A-283 | CH$_3$ | 3-ethyl-phenyl |
| A-284 | CH$_3$ | 4-ethyl-phenyl |
| A-285 | CH$_3$ | 2-isopropyl-phenyl |
| A-286 | CH$_3$ | 3-isopropyl-phenyl |
| A-287 | CH$_3$ | 4-isopropyl-phenyl |
| A-288 | CH$_3$ | 2-(2,2,2-trifluoroethyl)-phenyl |
| A-289 | CH$_3$ | 3-(2,2,2-trifluoroethyl)-phenyl |
| A-290 | CH$_3$ | 4-(2,2,2-trifluoroethyl)-phenyl |
| A-291 | CH$_3$ | 2-trifluoromethyl-phenyl |
| A-292 | CH$_3$ | 3-trifluoromethyl-phenyl |
| A-293 | CH$_3$ | 4-trifluoromethyl-phenyl |
| A-294 | CH$_3$ | 2-methoxy-phenyl |
| A-295 | CH$_3$ | 3-methoxy-phenyl |
| A-296 | CH$_3$ | 4-methoxy-phenyl |
| A-297 | CH$_3$ | 2-trifluoromethoxy-phenyl |
| A-298 | CH$_3$ | 3-trifluoromethoxy-phenyl |
| A-299 | CH$_3$ | 4-trifluoromethoxy-phenyl |
| A-300 | CH$_3$ | 2-difluoromethoxy-phenyl |
| A-301 | CH$_3$ | 3-difluoromethoxy-phenyl |
| A-302 | CH$_3$ | 4-difluoromethoxy-phenyl |
| A-303 | CH$_3$ | 2-(2,2,2-trifluoroethoxy)-phenyl |
| A-304 | CH$_3$ | 3-(2,2,2-trifluoroethoxy)-phenyl |
| A-305 | CH$_3$ | 4-(2,2,2-trifluoroethoxy)-phenyl |
| A-306 | CH$_3$ | 2-cyano-phenyl |
| A-307 | CH$_3$ | 3-cyano-phenyl |
| A-308 | CH$_3$ | 4-cyano-phenyl |
| A-309 | CH$_3$ | 2,3-difluoro-phenyl |
| A-310 | CH$_3$ | 2,4-difluoro-phenyl |
| A-311 | CH$_3$ | 2,5-difluoro-phenyl |
| A-312 | CH$_3$ | 2,6-difluoro-phenyl |
| A-313 | CH$_3$ | 2,3-dichloro-phenyl |
| A-314 | CH$_3$ | 2,4-dichloro-phenyl |
| A-315 | CH$_3$ | 2,5-dichloro-phenyl |
| A-316 | CH$_3$ | 2,6-dichloro-phenyl |

TABLE A-continued

| No | R¹ | R² |
|---|---|---|
| A-317 | CH₃ | 2-F-3-Cl-phenyl |
| A-318 | CH₃ | 2-F-4-Cl-phenyl |
| A-319 | CH₃ | 2-F-5-Cl-phenyl |
| A-320 | CH₃ | 2-F-6-Cl-phenyl |
| A-321 | CH₃ | 3-F-4-Cl-phenyl |
| A-322 | CH₃ | 3-F-5-Cl-phenyl |
| A-323 | CH₃ | 2-Cl-3-F-phenyl |
| A-324 | CH₃ | 2-Cl-4-F-phenyl |
| A-325 | CH₃ | 2-Cl-5-F-phenyl |
| A-326 | CH₃ | 3-Cl-4-F-phenyl |
| A-327 | CH₃ | 2-F-3-methyl-phenyl |
| A-328 | CH₃ | 2-F-4-methyl-phenyl |
| A-329 | CH₃ | 2-F-5-methyl-phenyl |
| A-330 | CH₃ | 2-F-6-methyl-phenyl |
| A-331 | CH₃ | 3-F-4-methyl-phenyl |
| A-332 | CH₃ | 3-F-5-methyl-phenyl |
| A-333 | CH₃ | 2-methyl-3-F-phenyl |
| A-334 | CH₃ | 2-methyl-4-F-phenyl |
| A-335 | CH₃ | 2-methyl-5-F-phenyl |
| A-336 | CH₃ | 3-methyl-4-F-phenyl |
| A-337 | CH₃ | 2-F-3-CF₃-phenyl |
| A-338 | CH₃ | 2-F-4-CF₃-phenyl |
| A-339 | CH₃ | 2-F-5-CF₃-phenyl |
| A-340 | CH₃ | 2-F-6-CF₃-phenyl |
| A-341 | CH₃ | 3-F-4-CF₃-phenyl |
| A-342 | CH₃ | 3-F-5-CF₃-phenyl |
| A-343 | CH₃ | 2-CF₃-3-F-phenyl |
| A-344 | CH₃ | 2-CF₃-4-F-phenyl |
| A-345 | CH₃ | 2-CF₃-5-F-phenyl |
| A-346 | CH₃ | 3-CF₃-4-F-phenyl |
| A-347 | CH₃ | 2-F-3-OMe-phenyl |
| A-348 | CH₃ | 2-F-4-OMe-phenyl |
| A-349 | CH₃ | 2-F-5-OMe-phenyl |
| A-350 | CH₃ | 2-F-6-OMe-phenyl |
| A-351 | CH₃ | 3-F-4-OMe-phenyl |
| A-352 | CH₃ | 3-F-5-OMe-phenyl |
| A-353 | CH₃ | 2-OMe-3-F-phenyl |
| A-354 | CH₃ | 2-OMe-4-F-phenyl |
| A-355 | CH₃ | 2-OMe-5-F-phenyl |
| A-356 | CH₃ | 3-OMe-4-F-phenyl |
| A-357 | CH₃ | 2-F-3-OCHF₂-phenyl |
| A-358 | CH₃ | 2-F-4-OCHF₂-phenyl |
| A-359 | CH₃ | 2-F-5-OCHF₂-phenyl |
| A-360 | CH₃ | 2-F-6-OCHF₂-phenyl |
| A-361 | CH₃ | 3-F-4-OCHF₂-phenyl |
| A-362 | CH₃ | 3-F-5-OCHF₂-phenyl |
| A-363 | CH₃ | 2-OCHF₂-3-F-phenyl |
| A-364 | CH₃ | 2-OCHF₂-4-F-phenyl |
| A-365 | CH₃ | 2-OCHF₂-5-F-phenyl |
| A-366 | CH₃ | 3-OCHF₂-4-F-phenyl |
| A-367 | CH₃ | 2-F-3-CN-phenyl |
| A-368 | CH₃ | 2-F-4-CN-phenyl |
| A-369 | CH₃ | 2-F-5-CN-phenyl |
| A-370 | CH₃ | 2-F-6-CN-phenyl |
| A-371 | CH₃ | 3-F-4-CN-phenyl |
| A-372 | CH₃ | 3-F-5-CN-phenyl |
| A-373 | CH₃ | 2-CN-3-F-phenyl |
| A-374 | CH₃ | 2-CN-4-F-phenyl |
| A-375 | CH₃ | 2-CN-5-F-phenyl |
| A-376 | CH₃ | 3-CN-4-F-phenyl |
| A-377 | CH₃ | 2-Cl-3-methyl-phenyl |
| A-378 | CH₃ | 2-Cl-4-methyl-phenyl |
| A-379 | CH₃ | 2-Cl-5-methyl-phenyl |
| A-380 | CH₃ | 2-Cl-6-methyl-phenyl |
| A-381 | CH₃ | 3-Cl-4-methyl-phenyl |
| A-382 | CH₃ | 3-Cl-5-methyl-phenyl |
| A-383 | CH₃ | 2-methyl-3-Cl-phenyl |
| A-384 | CH₃ | 2-methyl-4-Cl-phenyl |
| A-385 | CH₃ | 2-methyl-5-Cl-phenyl |
| A-386 | CH₃ | 3-methyl-4-Cl-phenyl |
| A-387 | CH₃ | 2-Cl-3-CF₃-phenyl |
| A-388 | CH₃ | 2-Cl-4-CF₃-phenyl |
| A-389 | CH₃ | 2-Cl-5-CF₃-phenyl |
| A-390 | CH₃ | 2-Cl-6-CF₃-phenyl |
| A-391 | CH₃ | 3-Cl-4-CF₃-phenyl |
| A-392 | CH₃ | 3-Cl-5-CF₃-phenyl |
| A-393 | CH₃ | 2-CF₃-3-Cl-phenyl |
| A-394 | CH₃ | 2-CF₃-4-Cl-phenyl |
| A-395 | CH₃ | 2-CF₃-5-Cl-phenyl |
| A-396 | CH₃ | 3-CF₃-4-Cl-phenyl |
| A-397 | CH₃ | 2-Cl-3-OMe-phenyl |
| A-398 | CH₃ | 2-Cl-4-OMe-phenyl |
| A-399 | CH₃ | 2-Cl-5-OMe-phenyl |
| A-400 | CH₃ | 2-Cl-6-OMe-phenyl |
| A-401 | CH₃ | 3-Cl-4-OMe-phenyl |
| A-402 | CH₃ | 3-Cl-5-OMe-phenyl |
| A-403 | CH₃ | 2-OMe-3-Cl-phenyl |
| A-404 | CH₃ | 2-OMe-4-Cl-phenyl |
| A-405 | CH₃ | 2-OMe-5-Cl-phenyl |
| A-406 | CH₃ | 3-OMe-4-Cl-phenyl |
| A-407 | CH₃ | 2-Cl-3-OCHF₂-phenyl |
| A-408 | CH₃ | 2-Cl-4-OCHF₂-phenyl |
| A-409 | CH₃ | 2-Cl-5-OCHF₂-phenyl |
| A-410 | CH₃ | 2-Cl-6-OCHF₂-phenyl |
| A-411 | CH₃ | 3-Cl-4-OCHF₂-phenyl |
| A-412 | CH₃ | 3-Cl-5-OCHF₂-phenyl |
| A-413 | CH₃ | 2-OCHF₂-3-Cl-phenyl |
| A-414 | CH₃ | 2-OCHF₂-4-Cl-phenyl |
| A-415 | CH₃ | 2-OCHF₂-5-Cl-phenyl |
| A-416 | CH₃ | 3-OCHF₂-4-Cl-phenyl |
| A-417 | CH₃ | 2-Cl-3-CN-phenyl |
| A-418 | CH₃ | 2-Cl-4-CN-phenyl |
| A-419 | CH₃ | 2-Cl-5-CN-phenyl |
| A-420 | CH₃ | 2-Cl-6-CN-phenyl |
| A-421 | CH₃ | 3-Cl-4-CN-phenyl |
| A-422 | CH₃ | 3-Cl-5-CN-phenyl |
| A-423 | CH₃ | 2-CN-3-Cl-phenyl |
| A-424 | CH₃ | 2-CN-4-Cl-phenyl |
| A-425 | CH₃ | 2-CN-5-Cl-phenyl |
| A-426 | CH₃ | 3-CN-4-Cl-phenyl |
| A-427 | CH₃ | CH₂-cyclopropyl |
| A-428 | CH₃ | CH₂-cyclopentyl |
| A-429 | CH₃ | CH₂-cyclohexyl |
| A-430 | CH₃ | CH₂-(4-quinolinyl) |
| A-431 | CH₃ | CH₂-(2-pyridyl) |
| A-432 | CH₃ | CH₂-(3-pyridyl) |
| A-433 | CH₃ | CH₂-(4-pyridyl) |
| A-434 | CH₃ | CH₂-(2-thienyl) |
| A-435 | CH₃ | CH₂-(3-thienyl) |
| A-436 | CH₃ | CH₂-(N-methyl-3-pyrazolyl) |
| A-437 | CH₃ | CH₂-(N-methyl-4-pyrazolyl) |
| A-438 | CH₃ | CH₂-(1-pyrazolyl) |
| A-439 | CH₃ | CH₂-(2-oxazolyl) |
| A-440 | CH₃ | CH₂-(4-oxazolyl) |
| A-441 | CH₃ | CH₂-(5-oxazolyl) |
| A-442 | CH₃ | CH₂-(2-(1,3,4-oxadiazolyl)) |
| A-443 | CH₃ | CH₂-(2-furyl) |
| A-444 | CH₃ | CH₂-(3-furyl) |
| A-445 | CH₃ | 3-hydroxypropyl |
| A-446 | CH₃ | CH₂-(N-methyl-3-pyrrolidinyl) |
| A-447 | CH₃ | 3-dimethylaminopropyl |
| A-448 | CH₃ | 2-dimethylaminoethyl |
| A-449 | CH₃ | 3-pyrrolidinyl |
| A-450 | CH₃ | benzyl |
| A-451 | CH₃ | (2-F-phenyl)methyl |
| A-452 | CH₃ | (3-F-phenyl)methyl |
| A-453 | CH₃ | (4-F-phenyl)methyl |
| A-454 | CH₃ | (2-Cl-phenyl)methyl |
| A-455 | CH₃ | (3-Cl-phenyl)methyl |
| A-456 | CH₃ | (4-Cl-phenyl)methyl |
| A-457 | CH₃ | (2-methyl-phenyl)methyl |
| A-458 | CH₃ | (3-methyl-phenyl)methyl |
| A-459 | CH₃ | (4-methyl-phenyl)methyl |
| A-460 | CH₃ | (2-methoxy-phenyl)methyl |
| A-461 | CH₃ | (3-methoxy-phenyl)methyl |
| A-462 | CH₃ | (4-methoxy-phenyl)methyl |
| A-463 | CH₃ | (2-cyano-phenyl)methyl |
| A-464 | CH₃ | (3-cyano-phenyl)methyl |
| A-465 | CH₃ | (4-cyano-phenyl)methyl |
| A-466 | CH₃ | (2,3-difluoro-phenyl)methyl |
| A-467 | CH₃ | (2,4-difluoro-phenyl)methyl |
| A-468 | CH₃ | (2,5-difluoro-phenyl)methyl |
| A-469 | CH₃ | (2,6-difluoro-phenyl)methyl |
| A-470 | CH₃ | (2,3-dichloro-phenyl)methyl |
| A-471 | CH₃ | (2,4-dichloro-phenyl)methyl |

TABLE A-continued

| No | R¹ | R² |
|---|---|---|
| A-472 | CH₃ | (2,5-dichloro-phenyl)methyl |
| A-473 | CH₃ | (2,6-dichloro-phenyl)methyl |

The compounds of formula I can be prepared according to methods or in analogy to methods as described in the prior art. The synthesis takes advantage of readily available starting materials that are known, commercially available or may be prepared according to conventional procedures starting from known compounds.

Compounds of the formula I can be prepared by reacting amides of type II with an appropriate sulfonation reagent, preferably Lawessons reagent, in an organic solvent, preferably at temperatures between 20° C. and 150° C., preferably at 110° C., as previously described (see for example Journal of Organic Chemistry, 2008, 73, 9102 or European Journal of Organic Chemistry, 2015, 30, 6687).

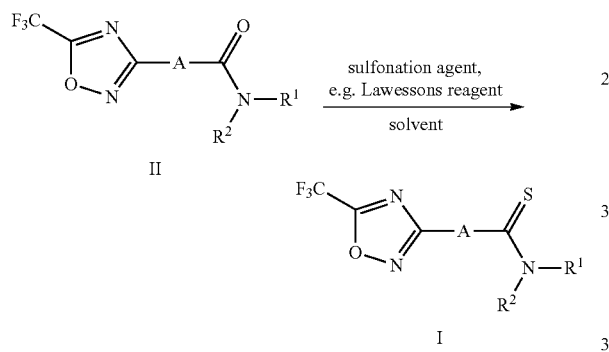

Compounds of the formula II can be prepared in analogy to methods described in WO 2015/185485 A1, for example by reacting acid chlorides of type II with the respective amine or its hydrochloride salt in an organic solvent, preferably in a non-polar hydrocarbon at temperatures between −20° C. and 40° C., preferably at 0° C. or at room temperature, as previously described (see for example Journal of the American Chemical Society, 2012, 134 (20), 8298 or Journal of the American Chemical Society, 2005, 127(38), 13150). If the hydrochloride salt is used, it may be appropriate to add an organic base, preferably an amine to liberate the free amine in situ.

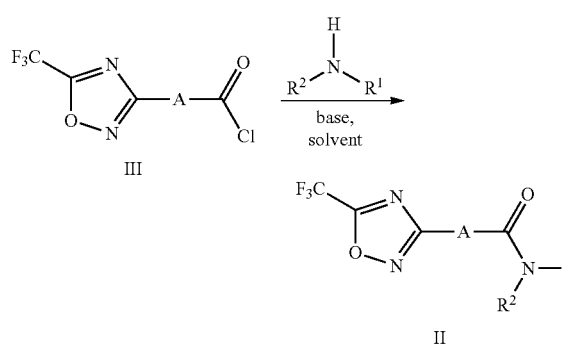

Compounds III may be accessed by reacting carboxylic acids of formula IV with an appropriate chlorinating agent, preferably thionyl chloride, either neat or in an organic solvent, preferably a non-polar hydrocarbon or a halocarbon. The reaction is best performed at elevated temperatures, preferably in the range of 40–100° C.

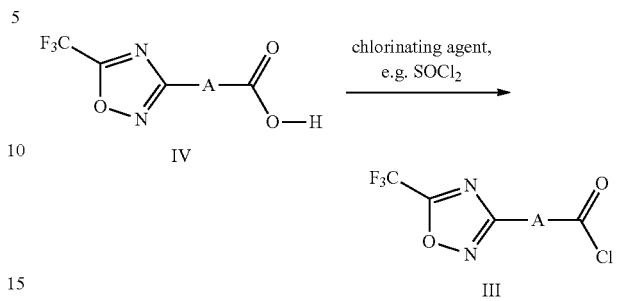

Compounds IV can be prepared by reacting amidines of formula V with trifluoroacetic anhydride in an organic solvent, e.g. dichloromethane, or THF at temperatures between 0° C. and 100° C., preferably at about 25° C., as previously described in WO 2013/008162.

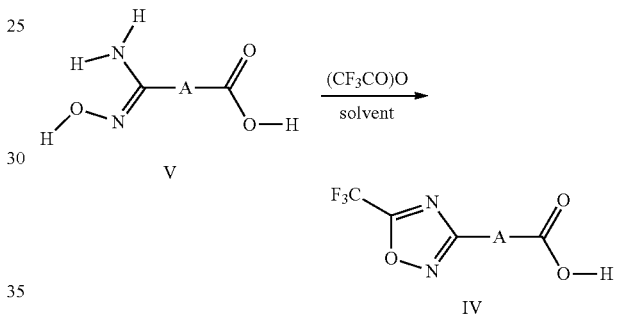

A skilled person will recognize that compounds of type IV can be accessed by treating nitriles of type V with hydroxylamine (or its HCl salt) in an organic solvent and in the presence of a base (for precedents see for example WO2009/074950, WO2006/013104, EP1932843).

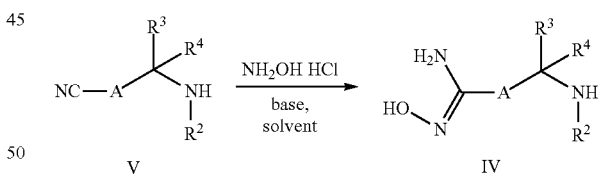

The compounds of the formula I or compositions comprising said compounds according to the invention are suitable as fungicides. They are distinguished by an outstanding effectiveness against a broad spectrum of phytopathogenic fungi, including soil-borne fungi, which derive especially from the following classes or are closely related to any of them: Ascomycota (Ascomycetes), for example, but not limited to the genus *Cocholiobolus*, *Colletotrichum*, *Fusarium*, *Microdochium*, *Penicillium*, *Phoma*, *Magnaporte*, *Zymoseptoria*, and *Pseudocercosporella*; Basdiomycota (Basidiomycetes), for example, but not limited to the genus *Phakospora*, *Puccinia*, *Rhizoctonia*, *Sphacelotheca*, *Tilletia*, *Typhula*, and *Ustilago*; Chytridiomycota (Chytndiomycetes), for example, but not limited to the genus *Chytridiales*, and *Synchytrium*; Deuteromycetes (syn. Fungi imperfecti), for example, but not limited to the genus *Ascochyta, Diplodia, Erysiphe, Fusarium, Phomopsis,* and *Pyrenophora*; Peronosporomycetes (syn. Oomycetes), for example but not limited to the genus *Peronospora, Pythium, Phytophthora*; Plasmodiophoromycetes, for example but not limited to the genus *Plasmodiophora*; Zygomycetes, for example, but not limited to the genus *Rhizopus*.

Some of the compounds of the formula I and the compositions according to the invention are systemically effective and they can be used in crop protection as foliar fungicides, fungicides for seed dressing and soil fungicides. Moreover, they are suitable for controlling harmful fungi, which inter alia occur in wood or roots of plants.

The compounds I and the compositions according to the invention are particularly important in the control of a multitude of phytopathogenic fungi on various cultivated plants, such as cereals, e. g. wheat, rye, barley, triticale, oats or rice; beet, e. g. sugar beet or fodder beet; fruits, such as pomes, stone fruits or soft fruits, e. g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called Stevia); natural rubber plants or ornamental and forestry plants, such as flowers, shrubs, broad-leaved trees or evergreens, e. g. conifers; and on the plant propagation material, such as seeds, and the crop material of these plants.

Preferably, compounds I and compositions thereof, respectively are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil.

These young plants may also be protected before transplantation by a total or partial treatment by immersion or pouring.

Preferably, treatment of plant propagation materials with compounds I and compositions thereof, respectively, is used for controlling a multitude of fungi on cereals, such as wheat, rye, barley and oats; rice, corn, cotton and soybeans.

The term "cultivated plants" is to be understood as including plants which have been modified by mutagenesis or genetic engineering in order to provide a new trait to a plant or to modify an already present trait.

The compounds I and compositions thereof, respectively, are particularly suitable for controlling the following plant diseases:

*Albugo* spp. (white rust) on ornamentals, vegetables (e. g. *A. candida*) and sunflowers (e. g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e. g. *A. solani* or *A. altemata*), tomatoes (e. g. *A. solani* or *A. altemata*) and wheat; *Aphanomyces* spp. on sugar beets and vegetables; *Ascochyta* spp. on cereals and vegetables, e. g. *A. tritici* (anthracnose) on wheat and *A. hordei* on barley; *Bipolaris* and *Drechslera* spp. (teleomorph: *Cochliobolus* spp.), e. g. Southern leaf blight (*D. maydis*) or Northern leaf blight (*B. zeicola*) on corn, e. g. spot blotch (*B. sorokiniana*) on cereals and e. g. *B. oryzae* on rice and turfs; *Blumeria* (formerly *Erysiphe*) *graminis* (powdery mildew) on cereals (e. g. on wheat or barley); *Botrytis cinerea* (teleomorph: *Botryotinia fuckliana*: grey mold) on fruits and berries (e. g. strawberries), vegetables (e. g. lettuce, carrots, celery and cabbages), rape, flowers, vines, forestry plants and wheat; Bremia lactucae (downy mildew) on lettuce; *Ceratocystis* (syn. *Ophiostoma*) spp. (rot or wilt) on broad-leaved trees and evergreens, e. g. *C. ulmi* (Dutch elm disease) on elms; *Cercospora* spp. (*Cercospora* leaf spots) on corn (e. g. Gray leaf spot: *C. zeae-maydis*), rice, sugar beets (e. g. *C. beticola*), sugar cane, vegetables, coffee, soybeans (e. g. *C. sojina* or *C. kikuchii*) and rice; *Cladosporium* spp. on tomatoes (e. g. *C. fulvum*: leaf mold) and cereals, e. g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e. g. *C. sativus*, anamorph: *B. sorokiniana*) and rice (e. g. *C. miyabeanus*, anamorph: *H. oryzae*); *Colletotrichum* (teleomorph: *Glomerella*) spp. (anthracnose) on cotton (e. g. *C. gossypii*), corn (e. g. *C. graminicola*: Anthracnose stalk rot), soft fruits, potatoes (e. g. *C. coccodes*: black dot), beans (e. g. *C. lindemuthianum*) and soybeans (e. g. *C. truncatum* or *C. gloeosporioides*); *Corticium* spp., e. g. *C. sasakii* (sheath blight) on rice; *Corynespora cassiicola* (leaf spots) on soybeans and ornamentals; *Cycloconium* spp., e. g. *C. oleaginum* on olive trees; *Cylindrocarpon* spp. (e. g. fruit tree canker or young vine decline, teleomorph: *Nectria* or *Neonectria* spp.) on fruit trees, vines (e. g. *C. liriodendri*, teleomorph: *Neonectria liriodendri*: Black Foot Disease) and ornamentals; *Dematophora* (teleomorph: *Roseliinia*) *necatrix* (root and stem rot) on soybeans; *Diaporthe* spp., e. g. *D. phaseolorum* (damping off) on soybeans; *Drechslera* (syn. *Helminthosporium*, teleomorph: *Pyrenophora*) spp. on corn, cereals, such as barley (e. g. *D. teres*, net blotch) and wheat (e. g. *D. tritici-repentis*: tan spot), rice and turf; Esca (dieback, apoplexy) on vines, caused by *Formitiporia* (syn. *Phellinus*) *punctata, F. mediterranea, Phaeomoniella chlamydospora* (earlier *Phaeoacremonium chlamydosporum*), *Phaeoacremonium aleophllum* and/or *Botryosphaeria obtuse; Elsinoe* spp. on pome fruits (*E. pyri*), soft fruits (*E. veneta*: anthracnose) and vines (*E. ampelina*: anthracnose); Entyloma *oryzae* (leaf smut) on rice; *Epicoccum* spp. (black mold) on wheat; *Erysiphe* spp. (powdery mildew) on sugar beets (*E. betae*), vegetables (e. g. *E. pisi*), such as cucurbits (e. g. *E. cichoracearum*), cabbages, rape (e. g. *E. cruciferarum*); *Eutypa lata* (*Eutypa* canker or dieback, anamorph: *Cytosporina lata*, syn. *Libertella blepharis*) on fruit trees, vines and ornamental woods; *Exserohllum* (syn. *Helminthosporium*) spp. on corn (e. g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e. g. wheat or barley), *F. oxysporum* on tomatoes, *F. solani* (f. sp. *glycines* now syn. *F. virguliforme*) and *F. tucumaniae* and *F. brasilierase* each causing sudden death syndrome on soybeans, and *F. verticillioides* on corn; *Gaeumannomyces graminis* (take-all) on cereals (e. g. wheat or barley) and corn; *Gibberella* spp. on cereals (e. g. *G. zeae*) and rice (e. g. *G. fufikuroi*: Bakanae disease); *Glomerella* cingulata on vines, pome fruits and other plants and *G. gossypii* on cotton; Grainstaining complex on rice; *Guignardia bidwellii* (black rot) on vines; *Gymnosporangium* spp. on rosaceous plants and junipers, e. g. *G. sabinae* (rust) on pears; *Helminthosporium* spp. (syn. *Drechslera*, teleomorph: *Cochliobolus*) on corn, cereals and rice; *Hemileia* spp., e. g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) n/vale (pink snow mold) on cereals (e. g. wheat or barley); *Microsphaera diffusa* (powdery mildew) on soybeans; *Monilinia* spp., e. g. *M. laxa*, *M. fructicola* and *M. fructigena* (bloom and twig blight, brown rot) on stone fruits and other rosaceous plants; *Mycosphaerella* spp. on cereals, bananas, soft fruits and ground nuts, such as e. g. *M. graminicola* (anamorph: *Septoria tritici*, *Septoria* blotch) on wheat or *M. fijiensis* (black Sigatoka disease) on bananas; *Peronospora* spp. (downy mildew) on cabbage (e. g. *P. brassicae*), rape (e. g. *P. parasitica*), onions (e. g. *P. destructor*), tobacco (*P. tabacina*) and soybeans (e. g. *P. manshurica*); *Phakopsora pachyrhizi* and *P. meibomiae* (soybean rust) on soybeans; *Phialophora* spp. e. g. on vines (e. g. *P. tracheiphlla* and *P. tetraspora*) and soybeans (e. g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e. g. *P. viticoia*: can and leaf spot) and soybeans (e. g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e. g. *P. capsici*), soybeans (e. g. *P. megasperma*, syn. *P. sojae*), potatoes and tomatoes (e. g. *P. infestans*: late blight) and broad-leaved trees (e. g. *P. ramorum*: sudden oak death); *Plasmodiophora brassicae* (club root) on cabbage, rape, radish and other plants; *Plasmopara* spp., e. g. *P. viticola* (grapevine downy mildew) on vines and *P. halstedii* on sunflowers; *Podosphaera* spp. (powdery mildew) on rosaceous plants, hop, pome and soft fruits, e. g. *P. leucotricha* on apples; *Polymyxa* spp., e. g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e. g. wheat or barley; *Pseudoperonospora* (downy mildew) on various plants, e. g. *P. cubensis* on cucurbits or *P. humili* on hop; *Pseudopezicula tracheiphila* (red fire disease or, 'rotbrenner', anamorph: *Phialophora*) on vines; *Puccinia* spp. (rusts) on various plants, e. g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye, *P. kuehnii* (orange rust) on sugar cane and *P. asparagi* on asparagus; *Pyrenophora* (anamorph: *Drechslera*) *tritici-repentis* (tan spot) on wheat or *P. teres* (net blotch) on barley; *Pyricularia* spp., e. g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e. g. *P. ultimum* or *P. aphanidermatum*); *Ramularia* spp., e. g. *R. colo-cygni* (*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e. g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e. g. *S. sclerotiorum*) and soybeans (e. g. *S. rolfsii* or *S. sclerotiorum*); *Septoria* spp. on various plants, e. g. *S. glycines* (brown spot) on soybeans, *S. tritici* (*Septoria* blotch) on wheat and S. (syn. *Stagonospora*) *nodorum* (*Stagonospora* blotch) on cereals; *Uncinula* (syn. *Erysiphe*) *necator* (powdery mildew, anamorph: *Oidium tuckeri*) on vines; *Setospaeria* spp. (leaf blight) on corn (e. g. *S. turcicum*, syn. *Helminthosporium turcicum*) and turf; *Sphacelotheca* spp. (smut) on corn, (e. g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e. g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e. g. *T. deformans* (leaf curl disease) on peaches and *T. pruni* (plum pocket) on plums; *Thielaviopsis* spp. (black root rot) on tobacco, pome fruits, vegetables, soybeans and cotton, e. g. *T. basicola* (syn. *Chalara elegans*); *Tilletia* spp. (common bunt or stinking smut) on cereals, such as e. g. *T. tritici*(syn. *T. caries*, wheat bunt) and *T. controversa* (dwarf bunt) on wheat; *Typhula incarnata* (grey snow mold) on barley or wheat; *Urocystis* spp., e. g. *U. occulta* (stem smut) on rye; *Uromyces* spp. (rust) on vegetables, such as beans (e. g. *U. appendiculatus*, syn. *U. phaseoli*) and sugar beets (e. g. *U. betae*); *Ustilago* spp. (loose smut) on cereals (e. g. *U. nuda* and *U. avaenae*), corn (e. g. *U. madis*: corn smut) and sugar cane; *Venturia* spp. (scab) on apples (e. g. *V. inaequalis*) and pears; and *Verticillium* spp. (wilt) on various plants, such as fruits and ornamentals, vines, soft fruits, vegetables and field crops, e. g. *V. dahliae* on strawberries, rape, potatoes and tomatoes. In a preferred embodiment the compounds I and compositions thereof, respectively, are particularly suitable for controlling the following plant diseases: *Puccinia* spp. (rusts) on various plants, for example, but not limited to *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye and *Phakopsoraceae* spp. on various plants, in particular *Phakopsora pachyrhizi* and *P. meibomiae* (soybean rust) on soybeans. The compounds I and compositions thereof, respectively, are also suitable for controlling harmful fungi in the protection of stored products or harvest and in the protection of materials. The term "protection of materials" is to be understood to denote the protection of technical and non-living materials, such as adhesives, glues, wood, paper and paperboard, textiles, leather, paint dispersions, plastics, cooling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocytis* spp., *Aureobasidium pullulans*, *Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp.,

*Cladosporium* spp., *Penicillium* spp., *Trichoderma* spp., *Alternaria* spp., *Paecilomyces* spp. and Zygomycetes such as *Mucor* spp., and in addition in the protection of stored products and harvest the following yeast fungi are worthy of note: *Candida* spp. and *Saccharomyces cerevisae*.

The method of treatment according to the invention can also be used in the field of protecting stored products or harvest against attack of fungi and microorganisms. According to the present invention, the term "stored products" is understood to denote natural substances of plant or animal origin and their processed forms, which have been taken from the natural life cycle and for which long-term protection is desired. Stored products of crop plant origin, such as plants or parts thereof, for example stalks, leafs, tubers, seeds, fruits or grains, can be protected in the freshly harvested state or in processed form, such as pre-dried, moistened, comminuted, ground, pressed or roasted, which process is also known as post-harvest treatment. Also falling under the definition of stored products is timber, whether in the form of crude timber, such as construction timber, electricity pylons and barriers, or in the form of finished articles, such as furniture or objects made from wood. Stored products of animal origin are hides, leather, furs, hairs and the like. The combinations according the present invention can prevent disadvantageous effects such as decay, discoloration or mold. Preferably "stored products" is understood to denote natural substances of plant origin and their processed forms, more preferably fruits and their processed forms, such as pomes, stone fruits, soft fruits and citrus fruits and their processed forms.

The compounds of formula I can be present in different crystal modifications whose biological activity may differ. They are likewise subject matter of the present invention.

The compounds I are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with compounds I as such or a composition comprising at least one compound I prophylactically either at or before planting or transplanting. The invention also relates to agrochemical compositions comprising an auxiliary and at least one compound I according to the invention.

An agrochemical composition comprises a fungicidally effective amount of a compound I. The term "effective amount" denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound I used.

The compounds I, their N-oxides and salts can be converted into customary types of agrochemical compositions, e. g. solutions, emulsions, suspensions, dusts, powders, pastes, granules, pressings, capsules, and mixtures thereof. Examples for composition types are suspensions (e. g. SC, OD, FS), emulsifiable concentrates (e. g. EC), emulsions (e. g. EW, EO, ES, ME), capsules (e. g. CS, ZC), pastes, pastilles, wettable powders or dusts (e. g. WP, SP, WS, DP, DS), pressings (e. g. BR, TB, DT), granules (e. g. WG, SG, GR, FG, GG, MG), insecticidal articles (e. g. LN), as well as gel formulations for the treatment of plant propagation materials such as seeds (e. g. GF). These and further compositions types are defined in the "Catalogue of pesticide formulation types and international coding system", Technical Monograph No. 2, 6$^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e. g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e. g. ethanol, propanol, butanol, benzyl alcohol, cyclohexanol; glycols; DMSO; ketones, e. g. cyclohexanone; esters, e. g. lactates, carbonates, fatty acid esters, gamma-butyrolactone; fatty acids; phosphonates; amines; amides, e. g. N-methyl pyrrolidone, fatty acid dimethyl amides; and mixtures thereof. Suitable solid carriers or fillers are mineral earths, e. g. silicates, silica gels, talc, kaolins, limestone, lime, chalk, clays, dolomite, diatomaceous earth, bentonite, calcium sulfate, magnesium sulfate, magnesium oxide; polysaccharides, e. g. cellulose, starch; fertilizers, e. g. ammonium sulfate, ammonium phosphate, ammonium nitrate, ureas; products of vegetable origin, e. g. cereal meal, tree bark meal, wood meal, nutshell meal, and mixtures thereof. Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylaryl sulfonates, diphenyl sulfonates, alpha-olefin sulfonates, lignin sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkyl naphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinyl pyrrolidone, vinyl alcohols, or vinyl acetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B—C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinyl amines or polyethylene amines.

Suitable adjuvants are compounds, which have a negligible or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e. g. xanthan gum, carboxymethyl cellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e. g. in red, blue, or green) are pigments of low water solubility and water-soluble dyes. Examples are inorganic colorants (e. g. iron oxide, titan oxide, iron hexacyanoferrate) and organic colorants (e. g. alizarin-, azo- and phthalocyanine colorants).

Suitable tackifiers or binders are polyvinyl pyrrolidones, polyvinyl acetates, polyvinyl alcohols, polyacrylates, biological or synthetic waxes, and cellulose ethers.

Examples for composition types and their preparation are:
i) Water-Soluble Concentrates (SL, LS)
10-60 wt % of a compound I and 5-15 wt % wetting agent (e. g. alcohol alkoxylates) are dissolved in water and/or in a water-soluble solvent (e. g. alcohols) ad 100 wt %. The active substance dissolves upon dilution with water.

ii) Dispersible Concentrates (DC)
5-25 wt % of a compound I and 1-10 wt % dispersant (e. g. polyvinyl pyrrolidone) are dissolved in organic solvent (e. g. cyclohexanone) ad 100 wt %. Dilution with water gives a dispersion.

iii) Emulsifiable Concentrates (EC)
15-70 wt % of a compound I and 5-10 wt % emulsifiers (e. g. calcium dodecylbenzenesulfonate and castor oil ethoxylate) are dissolved in water-insoluble organic solvent (e. g. aromatic hydrocarbon) ad 100 wt %. Dilution with water gives an emulsion.

iv) Emulsions (EW, EO, ES)
5-40 wt % of a compound I and 1-10 wt % emulsifiers (e. g. calcium dodecylbenzenesulfonate and castor oil ethoxylate) are dissolved in 20-40 wt % water-insoluble organic solvent (e. g. aromatic hydrocarbon). This mixture is introduced into water ad 100 wt % by means of an emulsifying machine and made into a homogeneous emulsion. Dilution with water gives an emulsion.

v) Suspensions (SC, OD, FS)
In an agitated ball mill, 20-60 wt % of a compound I are comminuted with addition of 2-10 wt % dispersants and wetting agents (e. g. sodium lignosulfonate and alcohol ethoxylate), 0.1-2 wt % thickener (e. g. xanthan gum) and water ad 100 wt % to give a fine active substance suspension. Dilution with water gives a stable suspension of the active substance. For FS type composition up to 40 wt % binder (e. g. polyvinyl alcohol) is added.

vi) Water-Dispersible Granules and Water-Soluble Granules (WG, SG)
50-80 wt % of a compound I are ground finely with addition of dispersants and wetting agents (e. g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS) 50-80 wt % of a compound I are ground in a rotor-stator mill with addition of 1-5 wt % dispersants (e. g. sodium lignosulfonate), 1-3 wt % wetting agents (e. g. alcohol ethoxylate) and solid carrier (e. g. silica gel) ad 100 wt %. Dilution with water gives a stable dispersion or solution of the active substance.

viii) Gel (GW, GF)
In an agitated ball mill, 5-25 wt % of a compound I are comminuted with addition of 3-10 wt % dispersants (e. g. sodium lignosulfonate), 1-5 wt % thickener (e. g. carboxymethyl cellulose) and water ad 100 wt % to give a fine suspension of the active substance. Dilution with water gives a stable suspension of the active substance.

ix) Microemulsion (ME)
5-20 wt % of a compound I are added to 5-30 wt % organic solvent blend (e. g. fatty acid dimethyl amide and cyclohexanone), 10-25 wt % surfactant blend (e. g. alcohol ethoxylate and arylphenol ethoxylate), and water ad 100%. This mixture is stirred for 1 h to produce spontaneously a thermodynamically stable microemulsion.

x) Microcapsules (CS)
An oil phase comprising 5-50 wt % of a compound I, 0-40 wt % water insoluble organic solvent (e. g. aromatic hydrocarbon), 2-15 wt % acrylic monomers (e. g. methylmethacrylate, methacrylic acid and a di- or triacrylate) are dispersed into an aqueous solution of a protective colloid (e. g. polyvinyl alcohol). Radical polymerization results in the formation of poly(meth)acrylate microcapsules. Alternatively, an oil phase comprising 5-50 wt % of a compound I according to the invention, 0-40 wt % water insoluble organic solvent (e. g. aromatic hydrocarbon), and an isocyanate monomer (e. g. diphenylmethene-4,4'-diisocyanatae) are dispersed into an aqueous solution of a protective colloid (e. g. polyvinyl alcohol). The addition of a polyamine (e. g. hexamethylenediamine) results in the formation of polyurea microcapsules. The monomers amount to 1-10 wt %. The wt % relate to the total CS composition.

xi) Dustable Powders (DP, DS)
1-10 wt % of a compound I are ground finely and mixed intimately with solid carrier (e. g. finely divided kaolin) ad 100 wt %.

xii) Granules (GR, FG)

0.5-30 wt % of a compound I is ground finely and associated with solid carrier (e. g. silicate) ad 100 wt %. Granulation is achieved by extrusion, spray-drying or fluidized bed.

xiii) Ultra-Low Volume Liquids (UL)

1-50 wt % of a compound I are dissolved in organic solvent (e. g. aromatic hydrocarbon) ad 100 wt %.

The compositions types i) to xiii) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, more preferably between 1 and 70%, and in particular between 10 and 60%, by weight of active substance. The active substances are employed in a purity of from 90% to 100%, preferably from 95% to 100% (according to NMR spectrum).

For the purposes of treatment of plant propagation materials, particularly seeds, solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC), and gels (GF) are usually employed. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying compound I and compositions thereof, respectively, onto plant propagation material, especially seeds, include dressing, coating, pelleting, dusting, and soaking as well as in-furrow application methods. Preferably, compound I or the compositions thereof, respectively, are applied on to the plant propagation material by a method such that germination is not induced, e. g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha. In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e. g. herbicides, insecticides, fungicides, growth regulators, safeners, biopesticides) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

A pesticide is generally a chemical or biological agent (such as pestidal active ingredient, compound, composition, virus, bacterium, antimicrobial or disinfectant) that through its effect deters, incapacitates, kills or otherwise discourages pests. Target pests can include insects, plant pathogens, weeds, mollusks, birds, mammals, fish, nematodes (roundworms), and microbes that destroy property, cause nuisance, spread disease or are vectors for disease. The term "pesticide" includes also plant growth regulators that alter the expected growth, flowering, or reproduction rate of plants; defoliants that cause leaves or other foliage to drop from a plant, usually to facilitate harvest; desiccants that promote drying of living tissues, such as unwanted plant tops; plant activators that activate plant physiology for defense of against certain pests; safeners that reduce unwanted herbicidal action of pesticides on crop plants; and plant growth promoters that affect plant physiology e.g. to increase plant growth, biomass, yield or any other quality parameter of the harvestable goods of a crop plant.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area. According to one embodiment, individual components of the composition according to the invention such as parts of a kit or parts of a binary or ternary mixture may be mixed by the user himself in a spray tank or any other kind of vessel used for applications (e. g. seed treater drums, seed pelleting machinery, knapsack sprayer) and further auxiliaries may be added, if appropriate.

Consequently, one embodiment of the invention is a kit for preparing a usable pesticidal composition, the kit comprising a) a composition comprising component 1) as defined herein and at least one auxiliary; and b) a composition comprising component 2) as defined herein and at least one auxiliary; and optionally c) a composition comprising at least one auxiliary and optionally a further active component 3) as defined herein.

I. SYNTHESIS

I.1) Preparation of 4-[(Z)—N'-hydroxycarbamimidoyl]benzoic acid

To a solution of the 4-cyano benzoic acid (500 g, 1.0 eq.) in a mixture of ethanol and water (5 liter/2 liter) was added hydroxylamine hydrochloride (495 g, 2.0 eq.) and potassium carbonate (751 g, 1.5 eq.). To the resulting mixture, 8-hydroxyquinoline (6.5 g, 0.1 eq.) was added and it was heated under reflux until HPLC indicated complete conversion of the starting material. After cooling to ambient temperature, water was added and the resulting precipitate was collected and dried to afford the title compound sufficiently pure to be used directly without further purification.

I.2) Preparation of 4-[5-(trifluoromethyl)-1,2,4-oxadiazol-3-yl]benzoic acid

A solution of 4-[(Z)—N'-hydroxycarbamimidoyl]benzoic acid (200 g, 1.0 eq.) in tetrahydrofurane (2.5 liter) was treated with trifluoroacetic anhydride (350 g, 1.5 eq.). The resulting mixture was stirred overnight at ambient temperature, before it was diluted with methyl tert-butyl ether and washed with a saturated aqueous solution of sodium bicarbonate. The organic layer was freed from solvent under reduced pressure to afford a crude product that was recrystallized from di-iso-propyl ether to furnish the title compound as light brown solid (220 g, 76%). 1H NMR (400 MHz, DMSO-d$_6$, 298 K): δ [ppm]=13.40 (br. s, 1H), 8.22-8.10 (m, 4H).

I.3) Preparation of 4-[5-(trifluoromethyl)-1,2,4-oxadiazol-3-yl]benzoyl chloride A 250 mL round-bottom flask was charged with 4-[5-(trifluoromethyl)-1,2,4-oxadiazol-3-yl]benzoic acid (20 g, 1.0 eq.) and thionyl chloride was added dropwise (50 mL, 5 eq.). To the suspension were added 2 drops of N,N-dimethylformamide and the mixture was warmed to gentle reflux for 2 h. When HPLC indicated complete conversion of the starting material, the mixture was cooled to room temperature and all volatiles were removed under reduced pressure. The residue was taken up in toluene and coevaporated to remove residual thionyl chloride. The title compound was isolated as light brown solid (20.7 g, 97%). $^1$H NMR (400 MHz, CDCl$_3$, 298 K): δ [ppm]=8.35-8.25 (m, 4H).

I.4) Preparation of N,N-dimethyl-4-[5-(trifluoromethyl)-1,2,4-oxadiazol-3-yl]benzamide A solution of 4-[5-(trifluoromethyl)-1,2,4-oxadiazol-3-yl] benzoyl chloride (1.5 g, 1.0 eq.) and dimethylamine (10.8 mL, 2M in THF, 4 eq.) in tetrahydrofuran (120 ml) was stirred over night, before it was quenched by the addition of water and the product was extracted into methylen chloride. The combined organic layers were successively washed with diluted aqueous solutions of hydrochloric acid and sodium bicarbonate, successively, dried over sodium sulfate and freed from solvent under reduced pressure to afford the title compound (1.46 g) that was used directly without further purification.

I.5) Preparation of N,N-dimethyl-4-[5-(trifluoromethyl)-1,2,4-oxadiazol-3-yl]benzenecarbothioamide (compound Ex-7)

To a solution of N,N-dimethyl-4-[5-(trifluoromethyl)-1, 2,4-oxadiazol-3-yl]benzamide (200 mg, 1.0 eq.) in toluene (2.5 mL) was added 2,4-Bis(4-methoxyphenyl)-2,4-dithioxo-1,3,2,4-dithiadiphosphetane (170 mg, 0.6 eq.). The resulting mixture was heated under reflux until HPLC indicated complete conversion of the starting material. After cooling to ambient temperature, the mixture was concentrated under reduced pressure. The residue was purified by flash chromatography to afford the title compound (0.10 g, 79%).
$^1$H NMR (400 MHz, CDCl$_3$, 298 K): δ [ppm]=8.16 (d, 2H), 7.48 (d, 2H), 3.61 (s, 3H), 3.20 (s, 3H).

The compounds listed in Table I were prepared in an analogous manner.

TABLE I

Compounds Ex-1 to Ex-29 of formula I, wherein A corresponds to subformula (A.2), wherein the group (A.2) is unsubstituted, and wherein the meaning of R$^1$ and R$^2$ are as defined in each line.

| Ex. no | R$^1$ | R$^2$ | HPLC R$_t$ (min)* | Melting point (C. °) |
|---|---|---|---|---|
| Ex-1 | CH$_3$ | benzyl | 1.387 | 63 |
| Ex-2 | CH$_3$ | cyclopropyl | 1.286 | 113 |
| Ex-3 | H | cyclopropyl | 1.170 | 135 |
| Ex-4 | H | CH$_3$ | 1.163 | 154 |
| Ex-5 | H | benzyl | 1.342 | 125 |
| Ex-6 | CH$_3$ | phenyl | 1.295 | 114 |
| Ex-7 | CH$_3$ | CH$_3$ | 1.129 | 82 |
| Ex-8 | H | 2-chloro-4-fluorophenyl | 1.279 | 142 |
| Ex-9 | CH$_3$ | 2-fluorobenzyl | 1.301 | — |
| Ex-10 | H | 4-fluorobenzyl | 1.273 | 133 |
| Ex-11 | H | 2-fluorophenyl | 1.250 | 123 |
| Ex-12 | H | 4-fluorophenyl | 1.266 | 186 |
| Ex-13 | H | 2-methylphenyl | 1.234 | 109 |
| Ex-14 | H | 4-methylphenyl | 1.263 | 186 |
| Ex-15 | H | 2,4-difluorophenyl | 1.239 | 164 |
| Ex-16 | H | phenyl | 1.335 | 165 |
| Ex-17 | H | ethyl | 1.246 | 134 |
| Ex-18 | H | CH$_2$cyclopropyl | 1.318 | 136 |
| Ex-19 | H | isopropyl | 1.288 | 90 |
| Ex-20 | CH$_3$ | isopropyl | 1.305 | 70 |
| Ex-21 | CH$_3$ | ethyl | 1.255 | 65 |
| Ex-22 | CH$_3$ | 2-fluorphenyl | 1.373 | — |
| Ex-23 | CH$_3$ | 4-fluorphenyl | 1.356 | 107 |
| Ex-24 | CH$_3$ | 2-methylphenyl | 1.389 | — |
| Ex-25 | CH$_3$ | 4-methylphenyl | 1.267 | — |
| Ex-26 | CH$_3$ | 2,4-difluorphenyl | 1.379 | 88 |
| Ex-27 | CH$_3$ | 4-fluorbenzyl | 1.377 | 106 |
| Ex-28 | CH$_3$ | CH$_2$CN | 1.197 | — |
| Ex-29 | CH$_3$ | CH$_2$-cyclopropyl | 1.392 | 69 |
| Ex-30 | H | 4-fluoro-2-methylphenyl | 1.465 | 144 |
| Ex-31 | CH$_3$ | 4-fluoro-2-methylphenyl | 1.403 | — |
| Ex-32 | H | 2-chlorophenyl | 1.347 | 104 |
| Ex-33 | CH$_3$ | 2-chlorophenyl | 1.393 | — |
| Ex-34 | H | 2-fluoro-4-methylphenyl | 1.343 | — |
| Ex-35 | CH$_3$ | 2-fluoro-4-methylphenyl | 1.422 | — |
| Ex-36 | H | 4-chlorophenyl | 1.363 | 188 |
| Ex-37 | CH$_3$ | 2-chloro-4-fluorophenyl | 1.421 | 118 |
| Ex-38 | CH$_3$ | 4-chlorophenyl | 1.412 | 139 |
| Ex-39 | H | tert-butyl | 1.346 | 97 |
| Ex-40 | H | 4-chloro-2-fluorophenyl | 1.416 | 143 |
| Ex-41 | CH$_3$ | 4-chloro-2-fluorophenyl | 1.461 | — |
| Ex-42 | H | 2,2-difluorocyclopropyl | 1.244 | 95 |
| Ex-43 | H | 2-ethylcyclopropyl | 1.378 | 94 |
| Ex-44 | H | 2-methylcyclopropyl | 1.317 | 132 |
| Ex-45 | H | 1-methylcyclopropyl | 1.304 | 111 |
| Ex-46 | H | 2-fluorobenzyl | 1.331 | 139 |

*HPLC: High Performance Liquid Chromatography; HPLC-column Kinetex XB C18 1.7µ (50 × 2.1 mm); eluent: acetonitrile/water + 0.1% trifluoroacetic acid (gradient from 5:95 to 100:0 in 1.5 min at 60° C., flow gradient from 0.8 to 1.0 ml/min in 1.5 min).
MS: Quadrupol Electrospray Ionisation, 80 V (positive mode).
R$_t$: retention time in minutes.

II. BIOLOGICAL EXAMPLES FOR FUNGICIDAL ACTIVITY

A. Glass House Trials

The fungicidal action of the compounds of formula I was demonstrated by the following experiments. Spray solutions were prepared in several steps. A mixture was prepared of acetone and/or dimethylsulfoxide and the wetting agent/emulsifier Wettol, which is based on ethoxylated alkylphenoles, in a relation (volume) solvent-emulsifier of 99 to 1 was added to 25 mg of the compound to give a total of 5 ml. Water was then added to a total volume of 100 ml. This stock solution was diluted with the described solvent-emulsifier-water mixture to the given concentration.

1. Curative Control of Soy Bean Rust on Soy Beans Caused by *Phakopsora pachyrhizi*

Leaves of pot-grown soy bean seedlings were inoculated with spores of *Phakopsora pachyrhizi*. To ensure the success of the artificial inoculation, the plants were transferred to a humid chamber with a relative humidity of about 95% and 20 to 24° C. for 24 h. The next day the plants were cultivated for 3 days in a greenhouse chamber at 23-27° C. and a relative humidity between 60 and 80%. Then the plants were sprayed to run-off with an aqueous suspension, containing the concentration of active ingredient or their mixture as described below. The plants were allowed to air-dry. Then the trial plants were cultivated for 14 days in a greenhouse chamber at 23-27° C. and a relative humidity between 60 and 80%. The extent of fungal attack on the leaves was visually assessed as % diseased leaf area.

In this test, the plants which had been treated with 32 ppm of the active compound Ex-1, Ex-2, Ex-3, Ex-4, Ex-5, Ex-7, Ex-8, Ex-9, Ex-11, Ex-12, Ex-13, Ex-15, Ex-16, Ex-17, Ex-18, Ex-19, Ex-20, Ex-21, Ex-28, Ex-32, Ex-39, Ex-43, Ex-44 and Ex-45 showed a diseased leaf area of at most 15%, whereas the untreated plants showed 90% diseased leaf area.

2. Protective Control of Soy Bean Rust on Soy Beans Caused by *Phakopsora pachyrhizi*

Leaves of pot-grown soy bean seedlings were sprayed to run-off with an aqueous suspension, containing the concentration of active ingredient or their mixture as described below. The plants were allowed to air-dry. The trial plants were cultivated for 2 days in a greenhouse chamber at 23-27° C. and a relative humidity between 60 and 80%. Then the plants were inoculated with spores of *Phakopsora pachyrhizi*. To ensure the success the artificial inoculation, the plants were transferred to a humid chamber with a relative humidity of about 95% and 20 to 24° C. for 24 h. The trial plants were cultivated for fourteen days in a greenhouse chamber at 23-27° C. and a relative humidity between 60 and 80%. The extent of fungal attack on the leaves was visually assessed as % diseased leaf area.

In this test, the plants which had been treated with 32 ppm of the active compound Ex-1, Ex-2, Ex-3, Ex-4, Ex-5, Ex-6, Ex-7, Ex-8, Ex-9, Ex-10, Ex-11, Ex-12, Ex-13, Ex-14, Ex-15, Ex-16, Ex-17, Ex-18, Ex-19, Ex-20, Ex-21, Ex-23, Ex-25, Ex-27, Ex-28, Ex-30, Ex-32, Ex-34, Ex-35, Ex-36, Ex-39, Ex-40, Ex-42, Ex-43, Ex-44 and Ex-45 showed a diseased leaf area of at most 15%, whereas the untreated plants showed 90% diseased leaf area.

3. Curative Control of Brown Rust on Wheat Caused by *Puccinia recondita*

The first two developed leaves of pot-grown wheat seedling were dusted with spores of *Puccinia recondita*. To ensure the success the artificial inoculation, the plants were transferred to a humid chamber without light and a relative humidity of 95 to 99% and 20 to 24° C. for 24 hours. The next day the plants were cultivated for 3 days in a greenhouse chamber at 20 to 24° C. and a relative humidity between 65 and 70%. Then the plants were sprayed to run-off with an aqueous suspension, containing the concentration of active ingredient or their mixture as described below. The plants were allowed to air-dry. Then the trial plants were cultivated for 8 days in a greenhouse chamber at 20 to 24° C. and a relative humidity between 65 and 70%. The extent of fungal attack on the leaves was visually assessed as % diseased leaf area.

In this test, the plants which had been treated with 63 ppm of the active compound Ex-1, Ex-2, Ex-3, Ex-4, Ex-9, Ex-10, Ex-17, Ex-18, Ex-19, Ex-21, Ex-28, Ex-29, Ex-43, Ex-44 and Ex-45 showed a diseased leaf area of at most 15%, whereas the untreated plants showed 90% diseased leaf area.

4. Preventative Control of Brown Rust on Wheat Caused by *Puccinia recondita*

The first two developed leaves of pot-grown wheat seedling were sprayed to run-off with an aqueous suspension, containing the concentration of active ingredient or their mixture as described below. Seven days later the plants were inoculated with spores of *Puccinia* recondite. To ensure the success the artificial inoculation, the plants were transferred to a humid chamber without light and a relative humidity of 95 to 99% and 20 to 24° C. for 24 hours. Then the trial plants were cultivated for 6 days in a greenhouse chamber at 20 to 24° C. and a relative humidity between 65 and 70%. The extent of fungal attack on the leaves was visually assessed as % diseased leaf area.

In this test, the plants which had been treated with 63 ppm of the active compound Ex-1, Ex-3, Ex-4, Ex-8, Ex-9, Ex-10, Ex-12, Ex-13, Ex-16, Ex-17, Ex-18, Ex-19, Ex-28, Ex-43, Ex-44 and Ex-45 showed a diseased leaf area of at most 15%, whereas the untreated plants showed 80% diseased leaf area.

The invention claimed is:
1. A compound of formula I, or an N-oxide or an agriculturally acceptable salt thereof,

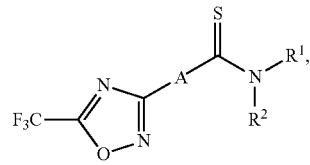

wherein:
A is phenyl or thiophenyl; and wherein the cyclic groups A are unsubstituted or substituted with 1, 2, 3 or 4 identical or different groups $R^A$; wherein
$R^A$ is OH, cyclopropyl, halogen, cyano, $diC_1$-$C_6$-alkylamino, $C_1$-$C_6$-alkyl, $C_1$-$C_6$-alkoxy, $C_1$-$C_6$-alkylthio, $C_2$-$C_6$-alkenyl, $C_2$-$C_6$-alkynyl, $C_3$-$C_8$-cycloalkyl or $C_3$-$C_8$-cycloalkoxy; and wherein any of the aliphatic or cyclic moieties are unsubstituted or substituted with 1, 2, 3 or 4 identical or different groups $R^a$; wherein
$R^a$ is halogen, cyano, $C_1$-$C_6$-alkyl, $C_1$-$C_6$-haloalkyl, $C_1$-$C_6$-alkoxy or $C_1$-$C_6$-haloalkoxy;
$R^1$, $R^2$ independently of each other are hydrogen, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkenyl, $C_1$-$C_4$-alkoxy, —C(═O)-($C_1$-$C_6$-alkyl), —C(═O)-($C_1$-$C_6$-alkoxy), phenyl-$C_1$-$C_4$-alkyl, heteroaryl-$C_1$-$C_4$-alkyl, $C_3$-$C_6$-cycloalkyl-$C_1$-$C_4$-alkyl, phenyl, naphthyl or a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms and wherein 1 or 2 carbon ring member atoms of the heterocycle may be replaced by 1 or 2 groups independently selected from —C(═O)— and —C(═S)—; and wherein the heteroaryl group in heteroaryl-$C_1$-$C_4$-alkyl is a 5- or 6-membered aromatic heterocycle, wherein the ring member atoms of the heterocyclic ring include besides carbon atoms 1, 2, 3 or 4 heteroatoms selected from N, O and S as ring member atoms; and wherein any of the above-mentioned aliphatic or cyclic groups are unsubstituted or substituted with 1, 2, 3 or up to the maximum possible number of identical or different groups $R^{1a}$;

or $R^1$ and $R^2$ together with the nitrogen atom to which they are bound form a saturated or partially unsaturated mono- or bicyclic 3- to 10-membered heterocycle, wherein the heterocycle includes beside one nitrogen atom and one or more carbon atoms 1, 2 or 3 heteroatoms independently selected from N, O and S as ring member atoms; and wherein one or two $CH_2$ groups of the heterocycle may be replaced by one or two groups independently selected from the group of —C(=O)— and —C(=S)—; and wherein the heterocycle is unsubstituted or substituted with 1, 2, 3, 4 or up to the maximum possible number of identical or different groups $R^{1a}$; wherein $R^{1a}$ is halogen, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $NHSO_2$-$C_1$-$C_4$-alkyl, —(C=O)$C_1$-$C_4$-alkyl, —C(=O)—$C_1$-$C_4$-alkoxy or $C_1$—$O_6$-alkylsulfonyl, hydroxy$C_1$-$C_4$-alkyl, —C(=O)—$NH_2$, —C(=O)—NH($C_1$-$C_4$-alkyl), $C_1$-$C_4$-alkylthio-$C_1$-$C_4$-alkyl, $C_1$-$C_4$-alkylamino-$C_1$-$C_4$-alkyl, di$C_1$-$C_4$-alkylamino-$C_1$-$C_4$-alkyl, aminocarbonyl-$C_1$-$C_4$-alkyl or $C_1$-$C_4$-alkoxy-$C_1$-$C_4$-alkyl;

with the proviso that $R^1$ and $R^2$ are not both hydrogen when (i) A is an unsubstituted phenyl ring and (ii) the trifluoromethyloxadiazole group and the —C(=S)$NR^2R^1$ group of formula I are attached to the phenyl ring para-relationship.

2. The compound of claim 1, wherein A is phenyl.

3. The compound of claim 1, wherein:
A is an unsubstituted phenyl ring;
the trifluoromethyloxadiazole group and the —C(=S)$NR^2$—$R^1$ group are situated on attached to the phenyl ring in a para-relationship;
$R^1$, $R^2$ independently of each other are hydrogen, $C_1$-$C_6$-alkyl, phenyl, or phenyl-$C_1$-$C_4$-alkyl, with the proviso that $R^1$ and $R^2$ are not both hydrogen.

4. The compound of claim 1, wherein $R^1$ is hydrogen or methyl and $R^2$ is methyl, ethyl, n-propyl, isopropyl, n-butyl, isobutyl or cyclopropyl; and wherein any of the aliphatic or cyclic groups are unsubstituted or substituted with 1, 2, 3, 4 or 5 or up to the maximum possible number of identical or different groups $R^{1a}$ as defined in claim 1.

5. The compound of claim 1, wherein $R^1$ is hydrogen or methyl and $R^2$ is phenyl-$C_1$-$C_4$-alkyl, heteroaryl-$C_1$-$C_4$-alkyl, $C_3$-$C_6$-cycloalkyl-$C_1$-$C_4$-alkyl; and wherein any of the aliphatic or cyclic groups are unsubstituted or substituted with 1, 2, 3, 4 or 5 up to the maximum possible number of identical or different groups $R^{1a}$.

6. The compound of claim 1, wherein $R^1$ is hydrogen or methyl and $R^2$ is phenyl; and wherein any of the aliphatic or cyclic groups are unsubstituted or substituted with 1, 2, 3, 4 or 5 up to the maximum possible number of identical or different groups $R^{1a}$.

7. An agrochemical composition, which comprises an auxiliary and at least one compound of claim 1.

8. An agrochemical composition of claim 7, wherein the auxiliary is selected from the group of ionic or non-ionic surfactants.

9. An agrochemical composition of claim 7 comprising at least one further pesticidally active substance selected from the group consisting of herbicides, safeners, fungicides, insecticides, and plant growth regulators.

10. An agrochemical composition of claim 7 further comprising seed, wherein the amount of the compound of formula I, or an N-oxide, or an agriculturally acceptable salt thereof, is from 0.1 g to 10 kg per 100 kg of seed.

11. A method for combating phytopathogenic harmful fungi, which process comprises treating the fungi or the plants, the soil or seeds to be protected against fungal attack, with an effective amount of at least one compound of formula I or an N-oxide or an agriculturally acceptable salt thereof as defined in claim 1.

12. The method of claim 11, wherein A is phenyl.

13. The method of claim 12, wherein the trifluoromethyloxadiazole group and the —C(=S)$NR^2$—$R^1$ group are situated on the phenyl ring to which they are attached in a para-relationship.

14. The method of claim 11, wherein $R^1$ is hydrogen or methyl and $R^2$ is methyl, ethyl, n-propyl, isopropyl, n-butyl, isobutyl or cyclopropyl; and wherein any of the aliphatic or cyclic groups are unsubstituted or substituted with 1, 2, 3, 4 or 5 or up to the maximum possible number of identical or different groups $R^{1a}$ as defined in claim 1.

15. The method of claim 11, wherein $R^1$ is hydrogen or methyl and $R^2$ is phenyl-$C_1$-$C_4$-alkyl, heteroaryl-$C_1$-$C_4$-alkyl, $C_3$-$C_6$-cycloalkyl-$C_1$-$C_4$-alkyl; and wherein any of the aliphatic or cyclic groups are unsubstituted or substituted with 1, 2, 3, 4 or 5 up to the maximum possible number of identical or different groups $R^{1a}$.

16. The method of claim 11, wherein $R^1$ is hydrogen or methyl and $R^2$ is phenyl; and wherein any of the aliphatic or cyclic groups are unsubstituted or substituted with 1, 2, 3, 4 or 5 up to the maximum possible number of identical or different groups $R^{1a}$.

17. A method for combating phytopathogenic harmful fungi, which process comprises treating the fungi or the plants, the soil or seeds to be protected against fungal attack, with an effective amount of the composition of claim 7.

18. A method for combating phytopathogenic harmful fungi, which process comprises treating the fungi or the plants, the soil or seeds to be protected against fungal attack, with an effective amount of the composition of claim 8.

19. A method for combating phytopathogenic harmful fungi, which process comprises treating the fungi or the plants, the soil or seeds to be protected against fungal attack, with an effective amount of the composition of claim 9.

20. A method for combating phytopathogenic harmful fungi, which process comprises treating the fungi or the plants, the soil or seeds to be protected against fungal attack, with an effective amount of the composition of claim 10.

* * * * *